US007455994B2

(12) United States Patent
Hevey et al.

(10) Patent No.: US 7,455,994 B2
(45) Date of Patent: Nov. 25, 2008

(54) METHODS FOR PRODUCING MARBURG VIRUS PROTEINS

(75) Inventors: Michael C. Hevey, Frederick, MD (US); Diane I. Negley, Frederick, MD (US); Peter Pushko, Frederick, MD (US); Jonathan F. Smith, Sabillasville, MD (US); Alan L. Schmaljohn, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 42 days.

(21) Appl. No.: 11/485,158

(22) Filed: Jul. 12, 2006

(65) Prior Publication Data

US 2006/0251681 A1    Nov. 9, 2006

Related U.S. Application Data

(62) Division of application No. 10/267,322, filed on Oct. 9, 2002, now Pat. No. 7,090,852, which is a division of application No. 09/336,910, filed on Jun. 21, 1999, now Pat. No. 6,517,842.

(60) Provisional application No. 60/091,403, filed on Jun. 29, 1998.

(51) Int. Cl.
*C12N 15/40* (2006.01)
(52) U.S. Cl. .................................................. 435/69.3
(58) Field of Classification Search ........................ None
See application file for complete search history.

(56) References Cited

U.S. PATENT DOCUMENTS 5,792,462 A * 8/1998 Johnston et al. .......... 424/199.1
5,811,407 A * 9/1998 Johnston et al. ................ 514/44
6,541,010 B1 * 4/2003 Johnston et al. .......... 424/199.1

OTHER PUBLICATIONS

Hevey et al (Virology 239:206-216, 1997).*
Becker et al (Virology 225:145-155, 1996).*
Pushko et al (Virology 239:389-401, 1997).*
Pushko et al (Vaccines 97, p. 253-258, 1997).*
Vanderzanden et al., "DNA Vaccines Expressing Either the GP or NP Genes of Ebola Virus Ptoect Mice from Lethal Challenge", Virology 245, 000-000 (1998), pp. 1-10.
Xu et al, "Immunization for Ebola Virus infection", Nature Medicine, vol. 4, No. 1, Jan. 1998, pp. 37-42.
Bray et al., "A mouse model for evaluatio nof prophylaxis and therapy of Ebola hemorrhagive fever", J. Infectious Diseases, 1998, 178:651-61.
Will et al., "Marburg virus gene 4 encosed the virion membrane protein, a Type I transmembrane glycoprotein", J. Virology, Mar. 1993, vol. 67, No. 3, p. 1203-1210.

Sanchez et al., "Sequence analysis of the Marburg virus nucleoprotein gene: comparison to Ebola virus and other non-segmented negative-strand RNA viruses", J. Gen. Virology (1992) 73:347-357.
Feldmann et al., "Glycosylation and oligomerization of the spike protein of Marburg virus", Virology 182, 353-356 (1991).
Feldmann et al., "Characterization of Filoviruses based on differences in structure and antigenicity of the virion glycoprotein", Virology 199, 469-473 (1994).
Johnson et al., "Lethal experimental infections of rhesus monkeys by aerosolized Ebola virus", Int. J. Exp. Path. (1995) 76:227-236.
Volchkov et al., "Processing of the Ebola virus glycoprotein by the proprotein convertase furin", PNAS USA, vol. 95, pp. 5762-5767 (May 1998).
Smith et al., "Fatal Human Disease from Vervet Monkeys", Preliminary Communications, The Lancet, No. 7256, Nov. 25, 1967, pp. 1119 and 1121.
Lupton et al., "New Activated Factor IX Product in Haemophilia", Letters to the Editor, The Lancet, Dec. 13, 1980, pp. 1294-1295.
Ignat'ev et al., "Comparative analysis of some immunological parameters of inactivated Marbug virus injected into guinea pigs", Voprosy Virusologii, No. 5, pp. 118-120, 1991.
Hevey et al., "Antigenicity and vaccine potential of Marburg virus glycoprotein expressed by Baculovirus recombinants", Virology 239:206-216 (1997).
Hevey et al., "Recombinant Marbug Virus glycoprotein subunit vaccine protects guinea pigs from lethal infection", Vaccines 97, 1997, pp. 93-98.
Connolly et al, "Pathogenesis of experimental Ebola virus infection in guinea pigs", J. Infectious Diseases, 1999: 179(suppl 1): S203-17.
Ignatyev et al, "Inactivated Marburg virus elicits a nonprotective immune response in Rhesus monkeys", J. Biotechnology 44 (1996) 111-118.
Caley et al, "Humoral, mucosal, and cellular immunity in response to a human immunodeficiency virus Type I immunogen expressed by a Venezuelan Equine Encephalitis virus vaccine vector", J. Virology, Apr. 1997, vol. 71, No. 4, p. 3031-3038.
Kiley et al, "Filoviridae: a taxonomic home of Marburg and Ebola Viruses?", Taxonomy, Intervirology 18:24-32, (1982).
Feldmann et al., "Marburg virus, a filovirus: messenger RNAs, gene order, and regulatory elements of the replication cycle", Virus Research, 24 (1992) 1-19.
Pushko et al., "Replicon-helper systems from attenuated Venezuelan Equine Encephalitis virus: expression of heterologous genes in vitro and immunization against heterologous pathogens in vivo", Virology 239:389-401 (1997).

(Continued)

*Primary Examiner*—Mary E Mosher
(74) *Attorney, Agent, or Firm*—Elizabeth Arwine

(57) ABSTRACT

Using the MBGV GP, NP, and virion proteins, a method and composition for use in inducing an immune response which is protective against infection with MBGV in nonhuman primates is described.

5 Claims, 12 Drawing Sheets

OTHER PUBLICATIONS

Xianzheng, et al. "Generation of cytotoxic and humoral immune responses by nonreplicative recombinant Semliki Forest virus", PNAS USA, vol. 92, p. 3009-3013, Mar. 1995.

Dubensky et al, "Sindbis virus DNA-based expression vectors: utility for in vrito and in vivo gene transfer", J. Virology, Jan. 1996, vol. 70, No. 1, pp. 508-519.

Pushko et al., "Venezuelan Equine Encephalitis virus replicon vector: immunogenicity studies with Ebola NP and GP genes in guinea pigs", Vaccines 97, 1997, p. 253-258.

Gilligan et al., "Assessment of protective immunity conferred by recombinant vaccinia viruses to guinea pigs challenged with Ebola virus", Vaccines 97 (1997), p. 87-92.

Feldmann and Klenk, "Marburg and Ebola Viruses", Advances in Virus Research, vol. 47, 1996, pp. 1-52.

Marburg Virus Disease, Ed. Martini and Siegert, Springer-Verlag, New York, Heidelberg, Berlin (1971), pp. 1-230.

Pattyn et al., "Isolation of Marburg-Like Virus from a Case of Haemorrhagic Fever in Zaire," The Lancet, Mar. 1977, p. 573-574.

* cited by examiner

Figure 6: Map of MBGV GP replicon plasmid.

Figure 7: Map of MBGV GPΔTM replicon plasmid

Figure 8: Map of MBGV NP replicon plasmid.

Figure 9: Map of MBGV VP40 replicon plasmid.

Figure 10: Map of MBGV VP35 replicon plasmid.

Figure 11: Map of MBGV VP30 replicon plasmid

Figure 12: Map of MBGV VP24 replicon plasmid.

SEQUENCE LISTING

<160> NUMBER OF SEQ ID NOS: 7

<210> SEQ ID NO 1
<211> LENGTH: 11460
<212> TYPE: DNA
<213> ORGANISM: Marburg Virus

<400> SEQUENCE: 1

```
agacacacaa aaacaagaga tgatgatttt gtgtatcata              40
taaataaaga agaatattaa cattgacatt gagacttgtc              80
agtcgtgtaa tattcttgaa gatatggatt tacacagttt             120
gttggagttg ggtacaaaac ccactgcccc tcatgtccgt             160
aataagaaag tgatattatt tgacacaaat catcaggtta             200
gtatctgtaa tcagataata gatgcaataa actcagggat             240
tgatcttgga gatctcctag aaggggtttt gctcacgttg             280
tgtgttgagc attactataa ttctgataag gataaattca             320
acacaagtcc tgtcgcgaag tacttacgtg atgcgggcta             360
tgaatttgat gtcatcaaga atgcagatgc aacccgcttt             400
ctggatgtga gtcctaatga acctcattac agccctttaa             440
ttctagccct taagacattg gaaagtactg aatctcagag              480
ggggagaatt gggctctttt tatcattttg cagtcttttc             520
ctcccaaaac ttgtcgtcgg agaccgagct agtatcgaaa             560
aggctttaag acaagtaaca gtgcatcaag aacaggggat             600
cgtcacatac cctaatcatt ggcttaccac aggccacatg             640
aaagtaattt tcgggatttt gaggtccagc ttcattttaa             680
agtttgtgtt gattcatcaa ggagtaaatt tggtgacagg             720
tcatgatgcc tatgacagta tcattagtaa ttcagtaggt             760
caaactagat tctcaggact tcttatcgtg aaaacagttc             800
tcgagttcat cttgcaaaaa actgattcag gggtgacact             840
acatcctttg gtgcggacct ccaaagtaaa aaatgaagtt             880
gctagtttca agcaggcgtt gagcaaccta gcccgacatg             920
gggaatacgc accatttgca cgggttctga atttatcagg             960
gattaacaac ctcgaacatg gactctatcc tcagctttca            1000
gcaattgcgc tgggtgtggc aacagcacac ggcagtacat            1040
tggctggtgt caatgttggc gaacaatatc aacaactacg            1080
agaggcggca catgatgcgg aagtaaaact acaaaggcga            1120
catgaacatc aggaaattca agctattgcc gaggatgacg            1160
aggaaaggaa gatattagaa caattccacc ttcagaaaac            1200
tgaaatcaca cacagtcaga cactagccgt cctcagccag            1240
aaacgagaaa aattagctcg tctcgctgca gaaattgaaa            1280
acaatattgt ggaagatcag ggatttaagc aatcacagaa            1320
tcgggtgtca cagtcgtttt tgaatgaccc tacacctgtg            1360
gaagtaacgg ttcaagccag gcccatgaat cgaccaactg            1400
ctctgcctcc cccagttgac gacaagattg agcatgaatc            1440
tactgaagat agctcttctt caagtagctt tgttgacttg            1480
aatgatccat ttgcactgct gaatgaggac gaggatactc            1520
ttgatgacag tgtcatgatc ccgggcacaa catcgagaga            1560
```

```
atttcaaggg attcctgaac cgccaagaca atcccaagac          1600
ctcaataaca gccaaggaaa gcaggaagat gaatccacaa          1640
atcggattaa gaaacagttt ctgagatatc aagaattgcc          1680
tcctgttcaa gaggatgatg aatcggaata cacaactgac          1720
tctcaagaaa gcatcgacca accaggatcc gacaatgaac          1760
aaggagttga tcttccacct cctccgttgt acgctcagga          1800
aaaaagacag gacccaatac agcacccagc agcaaaccct          1840
caggatccct tcggcagtat tggtgatgta aatggtgata          1880
tcttagaacc tataagatca ccttcttcac catctgctcc          1920
tcaggaagac acaaggatga gggaagccta tgaattgtcg          1960
cctgatttca caaatgatga ggataatcag cagaattggc          2000
cacaaagagt ggtgacaaag aagggtagaa ctttccttta          2040
tcctaatgat cttctgcaaa caaatcctcc agagtcactt          2080
ataacagccc tcgttgagga ataccaaaat cctgtctcag          2120
ctaaggagct tcaagcagat tggcccgaca tgtcatttga          2160
tgaaggagac atgttgcgat gaacttgtag tccagataac          2200
acagcacggt tactcactta tctattttga tatgactcat          2240
cctcagatca cagcaatcaa atttatttga atatttgaac          2280 cacctttttag tatcctatta cttgttacta ttgtgtgaga          2320
caacataagc catcaaataa caatcacggg caaggactgg          2360
gcatactatg gtggtcttag agcattgtcc agtgctacaa          2400
attctttttt caattgctat aattatacaa ctacaaacct          2440
ccatacattt gccgcaacac tgtaatcaac actgctgtat          2480
ctcttcttca agccatctga tttaacttaa taaacatgac          2520
ttgattcaaa gaatatactg acaatgttac tgtttgaatt          2560
tctcaagtgg tgcactatcc tactgttttg ctcagcttag          2600
tatattgtaa tatgtaagtg gactctcccc ttctcctctc          2640
gtgtattctt tataaatcac ttacttgata gaagttcgag          2680
tctactggtt tggagtttcc ttactctaat ggatgtaata          2720
attaactgtt ggcctagatg ataacagata tgaggttata          2760
taattactca tagtgtaaag tataattctt acctctgttt          2800
cttctgtttt cccttttcttt tataatatgc caattaagaa          2840
aaactaaaaa tcgaagaata ttaaagattt tctttaatat          2880
tcagaaaagg cttttttattc tattctttct ttttacaaac          2920
gtattgaaat agtaattctc acaatgtggg actcatcata          2960
catgcagcaa gtcagcgaag ggttgatgac tggaaaagta          3000
cccatagatc aagtgtttgg tgccaatccc ttagagaagt          3040
tatacaagag aagaaaacca aaaggcacag ttggactaca          3080
atgtagccct tgtctaatgt caaaggcgac aagtactgat          3120
gatattattt gggaccaact gatcgtgaag agaacactag          3160
```

```
ctgatctact tataccgata aataggcaga tatcagacat         3200
tcaaagcact ctaagcgaag taacaacaag agtccatgaa         3240
attgagcggc aattacatga gattacccca gttttaaaaa         3280
tgggaaggac actggaagca atttccaagg ggatgtcaga         3320
aatgttagcc aaatacgacc accttgtaat ttcaactgga         3360
agaaccactg caccagctgc tgcctttgat gcctacttaa         3400
atgagcatgg tgtccctccc cctcaacccg cgattttcaa         3440
agatcttggg gttgcccaac aagcttgtag taaggggacc         3480
atggttaaaa atgcaacaac agatgcagcc gacaagatgt         3520
caaaggttct tgaactcagt gaggaaacgt tctccaagcc         3560
aaacctttca gctaaggatt tagcccttttt attgtttacc         3600
catctacccg gcaacaacac tccattccat atcctagctc         3640
aggtcctttc aaaaattgct tacaagtcag gaaaatccgg         3680
agcattcttg gatgcatttc accagattct aagtgaagga         3720
gagaatgctc aggcggcatt aactcgacta agcagaacat         3760
ttgacgcttt ccttggagtg gttcctccag tgataagagt         3800
caaaaacttc caaacagtcc ctcgtccatc tcaaaaaagt         3840
cttcgggctg tccctccaaa tccaacaatt gacaaaggat         3880
gggtctgtgt ttattcatct gagcaaggtg aaacacgggc         3920
ccttaaaatc taattctcat tgttcatagt tgcaagggaa         3960
gtgatctttc cgagttgata caaagacact aaacatttca         4000
aaagcatgta tgtggacaaa acataattag accatcttaa         4040
ttggagtagt aatttatttc tgtcttaaat gtgattttca         4080
ctttaaaagc gttaaatgga gatagattaa tccttgaagt         4120
tactcttcta tatattatag agaaaccaat gttactaaca         4160
aaagggtct acctaacgca tatgattgag taatccgtat         4200
attttataaa ccaaacaatt aacttcttac tttttaagaa         4240
tcaactaaca acatagaaaa gacatttatc cttatgtaat         4280
cctcggctta gttgaaatta acttttgttg gacctcaaga         4320
cgcttattca tagtatatta tatgattttt tataagttta         4360
agatatctta aattataccc acaaaagata ctgttttaat         4400
taagaaaaac tatgaagaac attaagaaga tctttctttc         4440
gtagtgttct tttactggaa ggagtattcc aatttcagct         4480
tgttggatta attgttactt aaattgtcct ttttgaaatt         4520
aattcacaca aggtagttta aatttatatc caaaataaat         4560
tttgatatgg ccagttccag caattacaac acatacatgc         4600
aatacttgaa ctcccctcct tatgctgatc acggtgcaaa         4640
ccagttgatc ccggcggatc agctatcaaa tcagcagggt         4680
ataactccaa attcgtgggg tgatttaaac ctagatgatc         4720
agttcaaagg gaatgtctgc catgctttca ctttagaggc         4760
```

| | |
|---|---|
| aataattgac atatctgcat ataacgagcg aacagtcaaa | 4800 |
| ggcgttccgg catggctgcc tcttgggatt atgagcaatt | 4840 |
| ttgaatatcc tttagctcat actgtggccg cgttgctcac | 4880 |
| aggcagctat acaatcaccc aatttactca caacgggcaa | 4920 |
| aaattcgtcc gtgttaatcg acttggtaca ggaatcccag | 4960 |
| cacacccact cagaatgttg cgtgaaggaa atcaagcttt | 5000 |
| tattcagaat atggtgatcc ccaggaattt ttcaactaat | 5040 |
| caattcacct acaatctcac taatttagta ttgagtgtgc | 5080 |
| aaaaacttcc tgatgatgcc tggcgcccat ccaaggacaa | 5120 |
| attaattggg aacactatgc atcccgcagt ctccatccac | 5160 |
| ccgaatctgc cgcctattgt tctaccaaca gtcaagaagc | 5200 |
| aggcttatcg tcagcacaaa atcccaaca atggaccatt | 5240 |
| gctggccata tctggcatcc tccatcaact gagggtcgaa | 5280 |
| aaagtcccag agaagacgag cctgtttagg atctcgcttc | 5320 |
| ctgccgacat gttctcagta aaagagggta tgatgaagaa | 5360 |
| aaggggagaa aattcccccg tggtttattt tcaagcacct | 5400 |
| gagaacttcc ctttgaatgg cttcaataac agacaagttg | 5440 |
| tgctagcgta tgcgaatcca acgctcagtg ccgtttgaaa | 5480 |
| tgatgctcaa atgagacagg agtccatctg tataagaagt | 5520 |
| atggcttaaa tggatatttg tcaaattctt acaagattag | 5560 |
| tttgtattga tttcaacaat gctttaacct tacattgctg | 5600 |
| cttttaaatag ttgattaagc tgatcagctt gtaatatgta | 5640 |
| atctcttctg ggccatcaga tccataatgg gtttactaga | 5680 |
| ctatataaga gaaatagtaa tattttataa acaattcttg | 5720 |
| ctcagtttta ctgtgattta ataacatatg tcattgtgcc | 5760 |
| ctccattgct aagtcaactc aactgacgat aatactcctt | 5800 |
| ctgaaatagt aagaaaaact aatgaagaac attaattgct | 5840 |
| gggtaaaagt gattaatttc tttaaatttg accagaataa | 5880 |
| tattttgtca gtgaatatat tctcatatca cttgattaaa | 5920 |
| aacagaaaat taccctaaca tgaagaccac atgtttcctt | 5960 |
| atcagtctta tcttaattca agggacaaaa aatctcccca | 6000 |
| ttttagagat agctagtaat aatcaacccc aaaatgtgga | 6040 |
| ttcggtatgc tccggaactc tccagaagac agaagacgtc | 6080 |
| catctgatgg gattcacact gagtgggcaa aaagttgctg | 6120 |
| attccccttt ggaggcatcc aagcgatggg ctttcaggac | 6160 |
| aggtgtacct cccaagaatg ttgagtacac agaggggag | 6200 |
| gaagccaaaa catgctacaa tataagtgta acgatccct | 6240 |
| ctggaaaatc cttgctgtta gatcctccta ccaacatccg | 6280 |
| tgactatcct aaatgcaaaa ctatccatca tattcaaggt | 6320 |
| caaaaccctc atgcacaggg gatcgccctt catttatggg | 6360 |

```
gagcattttt tctgtatgat cgcattgcct ccacaacaat          6400
gtaccgaggc aaagtcttca ctgaagggaa catagcagct          6440
atgattgtca ataagacagt gcacaaaatg attttctcgc          6480
ggcaaggaca agggtaccgt catatgaatc tgacttctac          6520
taataaatat tggacaagta gtaacggaac gcaaacgaat          6560
gacactggat gtttcggcgc tcttcaagaa tacaattcta          6600
caaagaacca aacatgtgct ccgtccaaaa tacctccacc          6640
actgcccaca gcccgtccgg agatcaaact cacaagcacc          6680
ccaactgatg ccaccaaact caataccacg acccaagca           6720 gtgatgatga ggacctcgca acatccggct cagggtccgg          6760
agaacgagaa ccccacacaa cttctgatgc ggtcaccaag          6800
caagggcttt catcaacaat gccacccact ccctcaccac          6840
aaccaagcac gccacagcaa ggaggaaaca acacaaacca          6880
ttcccaagat gctgtgactg aactagacaa aaataacaca          6920
actgcacaac cgtccatgcc ccctcataac actaccacaa          6960
tctctactaa caaacctcc aaacacaact tcagcactct           7000
ctctgcacca ttacaaaaca ccaccaatga caacacacag          7040
agcacaatca ctgaaaatga gcaaaccagt gcccctcga           7080 taacaaccct gcctccaacg ggaaatccca ccacagcaaa          7120
gagcaccagc agcaaaaaag gccccgccac aacggcacca          7160
aacacgacaa atgagcattt caccagtcct cccccacc            7200 ccagctcgac tgcacaacat cttgtatatt tcagaagaaa          7240
gcgaagtatc ctctggaggg aaggcgacat gttccctttt          7280
ctggatgggt taataaatgc tccaattgat tttgacccag          7320
ttccaaatac aaaaacaatc tttgatgaat cctctagttc          7360
tggtgcctcg gctgaggaag atcaacatgc ctccccaat           7400 attagtttaa ctttatctta ttttcctaat ataaatgaga          7440
acactgccta ctctggagaa aatgagaatg attgtgatgc          7480
agagttaaga atttggagcg ttcaggagga tgacctggcc          7520
gcagggctca gttggatacc gttttttggc cctggaattg          7560
aaggacttta cactgctgtt ttaattaaaa atcaaaacaa          7600
tttggtctgc aggttgaggc gtctagccaa tcaaactgcc          7640
aaatccttgg aactcttatt gagagtcaca actgaggaaa          7680
gaacattctc cttaatcaat agacatgcta ttgactttct          7720
actcacaaga tgggaggaa catgcaaagt gcttggacct            7760
gattgttgca tcgggataga agacttgtcc aaaaatattt          7800
cagagcaaat tgaccaaatt aaaaaggacg aacaaaaaga          7840
ggggactggt tggggtctgg gtggtaaatg gtggacatcc          7880
gactggggtg ttcttactaa cttgggcatt ttgctactat          7920
tatccatagc tgtcttgatt gctctatcct gtatttgtcg          7960
```

| | |
|---|---|
| tatctttact aaatatatcg gataacgtta aatgtgtaat | 8000 |
| gattaggact ttaggacaat tgctactgag ccctttttcta | 8040 |
| atctactgaa atcaacttgg gagatttttta agaagctgat | 8080 |
| aacttaatgt gaatcaatag tttatgtatt atcgattatt | 8120 |
| atggtttgat attcaattgt tattattgtc aggagtgacc | 8160 |
| ttttctattt gatgcattaa tgttttaaac tacctcttaa | 8200 |
| gcctttgagg gcgtcccaat atgtgcgtag gggttaattt | 8240 |
| aaagggattt cttattgtac agttttctgt attacttatt | 8280 |
| tgggcttgaa gacatagtta agatttgccg aaatgctctc | 8320 |
| cagtcaattc catcccctct cagaaaagac gtgctgttca | 8360 |
| aagagtctta atttataacc aactattgca agaattaatt | 8400 |
| tacttttttcc gttatactta gttacattaa tcttttgact | 8440 |
| gttcagcatt attaacgact tgtcttaatt caatcgttcg | 8480 |
| gatgaaattc ataaggaaaa atgagcctcc ttcccctat | 8520 |
| tctgggctga gaaaatttct cttatccgcc taaaatcaga | 8560 |
| tctgttaggt catgggtcct tcataatctg tttgagcatg | 8600 |
| aatattgatg aaatgaccaa atgatagtgc atttgtatag | 8640 |
| actcaattat cctttattaa gaaaaagata aatagaacac | 8680 |
| aaagaattga caaaatttta ctttgattga ttttgcaagg | 8720 |
| agttataaaa atcttgaagg ataaattgtt ataaagtaga | 8760 |
| gtcgaagaac attaaatgtt ctttgttaga attattcatc | 8800 |
| taagttgttt ttgagtatat tcgcttcaat acaactcctc | 8840 |
| ttatatttga tttaagtttt aaaatgcaac aacctcgcgg | 8880 |
| aagaagtcga acccgcaacc accaagtcac accgactata | 8920 |
| tatcatgaaa ctcaattgcc ctccaaacct cattatacca | 8960 |
| attatcatcc acgtgcaaga tcgatgagct caacccgtag | 9000 |
| tagtgcagaa agtagtccca ccaatcatat tccccgtgct | 9040 |
| cgaccaccct caacattcaa cttatcgaaa cccctcctc | 9080 |
| ctccaaaaga catgtgcagg aacatgaaaa ttggattgcc | 9120 |
| gtgcgctgat cccacttgta atagagatca tgaccttgat | 9160 |
| aatctaacaa atcgtgaact tttgctattg atggcccgaa | 9200 |
| aaatgctccc caatacagac aagacccttta gaatgccgca | 9240 |
| ggactgtgga tcaccgtctc tttctaaagg tctctcaaaa | 9280 |
| gataaacagg agcaaacgaa agatgtgttg accttggaaa | 9320 |
| atctaggaca cattctgagc tatctccaca gatcagaaat | 9360 |
| tggaaattgg atgagacatc ttcgtgcagc attaagtctg | 9400 |
| acgtgtgctg gaattcgaaa gacgaataga tccttgatca | 9440 |
| acaccatgac agaattacac atgaaccatg aaaatctccc | 9480 |
| gcaagaccaa aacggtgtta tcaagcagac ctatacaggt | 9520 |
| attcaccttg acaaaggagg tcaattcgaa gccgccttat | 9560 |

| | |
|---|---|
| ggcaaggttg ggataagaga tcgatatctc tattcgtaca | 9600 |
| agcagcttta tatgtaatga acaatatccc ctgtgaatca | 9640 |
| tcaatcagtg tgcaagcctc atacgaatca ttttattctt | 9680 |
| cctcaaagtc aaggtaaagg acagtgatta ttgttcgaaa | 9720 |
| gttgacaatt tgatcacttt cagttttcag tttcaaccct | 9760 |
| tatcgcgaga cttgaataca atcctactaa cttcaataag | 9800 |
| tgaccccaaa ttcaagtttg ctgaaacgat agatgacaat | 9840 |
| gatcactagt tcattgtaaa ttactcgatc aaaatgttct | 9880 |
| taagctatct taagcttact gatgcggctc tgcttcactt | 9920 |
| ttcttttgat tttaaagcca tagctatatc taagtgtcta | 9960 |
| attaacaact tgtacctcta aggaaaaaca tgaagaacat | 10000 |
| taagaaaaag gatgttctta ttctttgact aaacctgcat | 10040 |
| attctttgtt gatacccttg agagacaact tttgacacca | 10080 |
| gatcacggat caagcacact tcaatcaagc accctaaatt | 10120 |
| ttcaatcata cacataataa ccattttagt agcgtggcct | 10160 |
| ttcagtacag tctaggtgat tgttgaaaga cttccaagca | 10200 |
| tggcagaatt atcaacgcgt tacaacttgc ctgcaaatgt | 10240 |
| tacgaaaaat agtataaatc ttgaccttaa ttccacagca | 10280 |
| cgatggataa aagaacccag tgttgggggc tggacagtga | 10320 |
| agtggggaaa ctttgttttc catataccaa atactggaat | 10360 |
| gacattgttg catcatttaa agtctaactt cgttgttcca | 10400 |
| gagtggcaac aaacaaggaa tctattctcc cacctcttta | 10440 |
| aaaacccaaa atcaacaatt atagaaccgt ttttggccct | 10480 |
| gaggattttg cttggagttg ctttgaagga tcaagaatta | 10520 |
| cagcaatcat tgattcctgg atttagatct attgttcata | 10560 |
| tgctatcaga atggctgctc ctggaggtca cgtcggcaat | 10600 |
| ccatattagc cctaatctgt tgggaatcta tttgacttca | 10640 |
| gacatgttta aaattctgat ggcaggtgtg aaaaatttct | 10680 |
| tcaataagat gttcactctt catgttgtaa atgaccacgg | 10720 |
| aaaacccagc agtattgaaa taagttaac tggacaacag | 10760 |
| atcattatca ctcgtgttaa tatggggttt ctagtggaag | 10800 |
| tcaggaggat tgatattgaa ccttgctgtg gtgagacagt | 10840 |
| cctctcagaa tcagttgttt ttggactagt ggctgaggca | 10880 |
| gttctaagag aacacagtca aatggagaag ggccaacctc | 10920 |
| tcaatctgac acaatacatg aacagcaaaa ttgctatata | 10960 |
| agtggcttaa attagcatgg gtattcctag ttcgaccaca | 11000 |
| taataatgtt ggaggcacag tacattatag ttaattgtct | 11040 |
| tgtatactaa gggatatacc taacctgatt tatatttact | 11080 |
| ggtataaaat agtagcatca tcttattgaa tagttatcat | 11120 |
| acaataggct gttcctataa tctgattgtg agattataaa | 11160 |

-continued

| | |
|---|---|
| cttgtagaat taccgtgggt cacaactgtt gcatatcctc | 11200 |
| caaaatatat cttttgcaag tgatgtgtgc ttgaatactt | 11240 |
| cgatataata catactaata acgattgatt aagaaaaatc | 11280 |
| aatgatggat attaaatgtc catcaagcaa gtgttgtaga | 11320 |
| ataccagggg tttcacaggc tgctaaactt actaaatttt | 11360 |
| acataggatt atataattct tttcgataca cgttatatct | 11400 |
| ttagcaaagt gaggaaaaca gctttatcat gttagatgcc | 11440 |
| agttatccat tttaagtgaa | 11460 |

<210> SEQ ID NO 2
<211> LENGTH: 681
<212> TYPE: PRT
<213> ORGANISM: Marburg Virus

<400> SEQUENCE: 2

```
Met Lys Thr Thr Cys Phe Leu Ile Ser Leu Ile Leu Ile Gln Gly
1               5                  10                 15

Thr Lys Asn Leu Pro Ile Leu Glu Ile Ala Ser Asn Asn Gln Pro
                20                 25                 30

Gln Asn Val Asp Ser Val Cys Ser Gly Thr Leu Gln Lys Thr Glu
                35                 40                 45

Asp Val His Leu Met Gly Phe Thr Leu Ser Gly Gln Lys Val Ala
                50                 55                 60

Asp Ser Pro Leu Glu Ala Ser Lys Arg Trp Ala Phe Arg Thr Gly
                65                 70                 75

Val Pro Pro Lys Asn Val Glu Tyr Thr Glu Gly Glu Glu Ala Lys
                80                 85                 90

Thr Cys Tyr Asn Ile Ser Val Thr Asp Pro Ser Gly Lys Ser Leu
                95                 100                105

Leu Leu Asp Pro Pro Thr Asn Ile Arg Asp Tyr Pro Lys Cys Lys
                110                115                120

Thr Ile His His Ile Gln Gly Gln Asn Pro His Ala Gln Gly Ile
                125                130                135

Ala Leu His Leu Trp Gly Ala Phe Phe Leu Tyr Asp Arg Ile Ala
                140                145                150

Ser Thr Thr Met Tyr Arg Gly Lys Val Phe Thr Glu Gly Asn Ile
                155                160                165

Ala Ala Met Ile Val Asn Lys Thr Val His Lys Met Ile Phe Ser
                170                175                180

Arg Gln Gly Gln Gly Tyr Arg His Met Asn Leu Thr Ser Thr Asn
                185                190                195

Lys Tyr Trp Thr Ser Ser Asn Gly Thr Gln Thr Asn Asp Thr Gly
                200                205                210

Cys Phe Gly Ala Leu Gln Glu Tyr Asn Ser Thr Lys Asn Gln Thr
                215                220                225

Cys Ala Pro Ser Lys Ile Pro Pro Pro Leu Pro Thr Ala Arg Pro
                230                235                240

Glu Ile Lys Leu Thr Ser Thr Pro Thr Asp Ala Thr Lys Leu Asn
                245                250                255

Thr Thr Asp Pro Ser Ser Asp Asp Glu Asp Leu Ala Thr Ser Gly
                260                265                270
```

-continued

```
Ser Gly Ser Gly Glu Arg Glu Pro His Thr Thr Ser Asp Ala Val
            275                 280                 285

Thr Lys Gln Gly Leu Ser Ser Thr Met Pro Pro Thr Pro Ser Pro
            290                 295                 300

Gln Pro Ser Thr Pro Gln Gln Gly Gly Asn Asn Thr Asn His Ser
            305                 310                 315

Gln Asp Ala Val Thr Glu Leu Asp Lys Asn Asn Thr Thr Ala Gln
            320                 325                 330

Pro Ser Met Pro Pro His Asn Thr Thr Thr Ile Ser Thr Asn Asn
            335                 340                 345

Thr Ser Lys His Asn Phe Ser Thr Leu Ser Ala Pro Leu Gln Asn
            350                 355                 360

Thr Thr Asn Asp Asn Thr Gln Ser Thr Ile Thr Glu Asn Glu Gln
            365                 370                 375

Thr Ser Ala Pro Ser Ile Thr Thr Leu Pro Pro Thr Gly Asn Pro
            380                 385                 390

Thr Thr Ala Lys Ser Thr Ser Lys Lys Gly Pro Ala Thr Thr
            395                 400                 405

Ala Pro Asn Thr Thr Asn Glu His Phe Thr Ser Pro Pro Pro Thr
            410                 415                 420

Pro Ser Ser Thr Ala Gln His Leu Val Tyr Phe Arg Arg Lys Arg
            425                 430                 435

Ser Ile Leu Trp Arg Glu Gly Asp Met Phe Pro Phe Leu Asp Gly
            440                 445                 450

Leu Ile Asn Ala Pro Ile Asp Phe Asp Pro Val Pro Asn Thr Lys
            455                 460                 465

Thr Ile Phe Asp Glu Ser Ser Ser Ser Gly Ala Ser Ala Glu Glu
            470                 475                 480

Asp Gln His Ala Ser Pro Asn Ile Ser Leu Thr Leu Ser Tyr Phe
            485                 490                 495

Pro Asn Ile Asn Gly Asn Thr Ala Tyr Ser Gly Glu Asn Glu Asn
            500                 505                 510

Asp Cys Asp Ala Glu Leu Arg Ile Trp Ser Val Gln Glu Asp Asp
            515                 520                 525

Leu Ala Ala Gly Leu Ser Trp Ile Pro Phe Phe Gly Pro Gly Ile
            530                 535                 540

Glu Gly Leu Tyr Thr Ala Val Leu Ile Lys Asn Gln Asn Asn Leu
            545                 550                 555

Val Cys Arg Leu Arg Arg Leu Ala Asn Gln Thr Ala Lys Ser Leu
            560                 565                 570

Glu Leu Leu Leu Arg Val Thr Thr Glu Glu Arg Thr Phe Ser Leu
            575                 580                 585

Ile Asn Arg His Ala Ile Asp Phe Leu Leu Thr Arg Trp Gly Gly
            590                 595                 600

Thr Cys Lys Val Leu Gly Pro Asp Cys Cys Ile Gly Ile Glu Asp
            605                 610                 615

Leu Ser Lys Asn Ile Ser Glu Gln Ile Asp Gln Ile Lys Lys Asp
            620                 625                 630

Glu Gln Lys Glu Gly Thr Gly Trp Gly Leu Gly Gly Lys Trp Trp
            635                 640                 645

Thr Ser Asp Trp Gly Val Leu Thr Asn Leu Gly Ile Leu Leu Leu
            650                 655                 660
```

```
Leu Ser Ile Ala Val Leu Ile Ala Leu Ser Cys Ile Cys Arg Ile
            665                 670                 675

Phe Thr Lys Tyr Ile Gly
            680

<210> SEQ ID NO 3
<211> LENGTH: 693
<212> TYPE: PRT
<213> ORGANISM: Marburg Virus

<400> SEQUENCE: 3

Met Asp Leu His Ser Leu Leu Glu Leu Gly Thr Pro Thr Ala Pro
  1               5                  10                  15

His Val Arg Asn Lys Lys Val Ile Leu Phe Asp Thr Asn His Gln
             20                  25                  30

Val Ser Ile Cys Asn Gln Ile Ile Asp Ala Ile Asn Ser Gly Ile
             35                  40                  45

Asp Leu Gly Asp Leu Leu Glu Gly Gly Leu Leu Thr Leu Cys
             50                  55                  60

Val Glu His Tyr Tyr Asn Ser Asp Lys Asp Lys Phe Asn Thr Ser
             65                  70                  75

Pro Val Ala Lys Tyr Leu Arg Asp Ala Gly Tyr Glu Phe Asp Val
             80                  85                  90

Ile Lys Asn Ala Asp Ala Thr Arg Phe Leu Asp Val Ser Pro Asn
             95                 100                 105

Glu Pro His Tyr Ser Pro Leu Ile Leu Ala Leu Lys Thr Leu Glu
            110                 115                 120

Ser Thr Glu Ser Gln Arg Gly Arg Ile Gly Leu Phe Leu Ser Phe
            125                 130                 135

Cys Ser Leu Phe Leu Pro Lys Leu Val Val Gly Asp Arg Ala Ser
            140                 145                 150

Ile Glu Lys Ala Leu Arg Gln Val Thr Val His Gln Glu Gln Gly
            155                 160                 165

Ile Val Thr Tyr Tyr Pro Asn His Trp Leu Thr Thr Gly His Met
            170                 175                 180

Lys Val Ile Phe Gly Ile Leu Arg Ser Ser Phe Ile Leu Lys Phe
            185                 190                 195

Val Leu Ile His Gln Gly Val Asn Leu Val Thr Gly His Asp Ala
            200                 205                 210

Tyr Asp Ser Ile Ile Ser Asn Ser Val Gly Gln Thr Arg Phe Ser
            215                 220                 225

Gly Leu Leu Ile Val Lys Thr Val Leu Glu Phe Ile Leu Gln Lys
            230                 235                 240

Thr Asp Ser Gly Val Thr Leu His Pro Leu Val Arg Thr Ser Lys
            245                 250                 255

Val Lys Asn Glu Val Ala Ser Phe Lys Gln Ala Leu Ser Asn Leu
            260                 265                 270

Ala Arg His Gly Glu Tyr Ala Pro Phe Ala Arg Val Leu Asn Leu
            275                 280                 285

Ser Gly Ile Asn Asn Leu Glu His Gly Leu Tyr Pro Gln Leu Ser
            290                 295                 300

Ala Ile Ala Leu Gly Val Ala Thr Ala His Gly Ser Thr Leu Ala
            305                 310                 315

Gly Val Asn Val Gly Glu Gln Tyr Glu Glu Leu Arg Glu Ala Ala
            320                 325                 330
```

```
His Asp Ala Glu Val Lys Leu Gln Arg Arg His Glu His Gln Glu
            335                 340                 345

Ile Gln Ala Ile Ala Glu Asp Asp Glu Arg Lys Ile Leu Glu
            350                 355                 360

Gln Phe His Leu Gln Lys Thr Glu Ile Thr His Ser Gln Thr Leu
            365                 370                 375

Ala Val Leu Ser Gln Lys Arg Glu Lys Leu Ala Arg Leu Ala Ala
            380                 385                 390

Glu Ile Glu Asn Asn Ile Val Glu Asp Gln Gly Phe Lys Gln Ser
            395                 400                 405

Gln Asn Arg Val Ser Gln Ser Phe Leu Asn Asp Pro Thr Pro Val
            410                 415                 420

Glu Val Thr Val Gln Ala Arg Pro Met Asn Arg Pro Thr Ala Leu
            425                 430                 435

Pro Pro Pro Val Asp Asp Lys Ile Glu His Glu Ser Thr Glu Asp
            440                 445                 450

Ser Ser Ser Ser Ser Ser Phe Val Asp Leu Asn Asp Pro Phe Ala
            455                 460                 465

Leu Leu Asn Glu Asp Glu Asp Thr Leu Asp Asp Ser Val Met Ile
            470                 475                 480

Pro Gly Thr Thr Ser Arg Glu Phe Gln Gly Ile Pro Glu Pro Pro
            485                 490                 495

Arg Gln Ser Gln Asp Leu Asn Asn Ser Gln Gly Lys Gln Glu Asp
            500                 505                 510

Glu Ser Thr Asn Arg Ile Lys Lys Gln Phe Leu Arg Tyr Gln Glu
            515                 520                 525

Leu Pro Pro Val Gln Glu Asp Asp Glu Ser Glu Tyr Thr Thr Asp
            530                 535                 540

Ser Gln Glu Ser Ile Asp Gln Pro Gly Ser Asp Asn Glu Gln Gly
            545                 550                 555

Val Asp Leu Pro Pro Pro Leu Tyr Ala Gln Glu Lys Arg Gln
            560                 565                 570

Asp Pro Ile Gln His Pro Ala Ala Asn Pro Gln Asp Pro Phe Gly
            575                 580                 585

Ser Ile Gly Asp Val Asn Gly Asp Ile Leu Glu Pro Ile Arg Ser
            590                 595                 600

Pro Ser Ser Pro Ser Ala Pro Gln Glu Asp Thr Arg Met Arg Glu
            605                 610                 615

Ala Tyr Glu Leu Ser Pro Asp Phe Thr Asn Asp Glu Asp Asn Gln
            620                 625                 630

Gln Asn Trp Pro Gln Arg Val Val Thr Lys Lys Gly Arg Thr Phe
            635                 640                 645

Leu Tyr Pro Asn Asp Leu Leu Gln Thr Asn Pro Pro Glu Ser Leu
            650                 655                 660

Ile Thr Ala Leu Val Glu Glu Tyr Gln Asn Pro Val Ser Ala Lys
            665                 670                 675

Glu Leu Gln Ala Asp Trp Pro Asp Met Ser Phe Asp Glu Gly Asp
            680                 685                 690

Met Leu Arg

<210> SEQ ID NO 4
<211> LENGTH: 303
<212> TYPE: PRT
<213> ORGANISM: Marburg Virus
```

-continued

```
<400> SEQUENCE: 4

Met Ala Ser Ser Ser Asn Tyr Asn Thr Tyr Met Gln Tyr Leu Asn
 1               5                  10                  15

Ser Pro Pro Tyr Ala Asp His Gly Ala Asn Gln Leu Ile Pro Ala
                20                  25                  30

Asp Gln Leu Ser Asn Gln Gln Gly Ile Thr Pro Asn Tyr Val Gly
                35                  40                  45

Asp Leu Asn Leu Asp Asp Gln Phe Lys Gly Asn Val Cys His Ala
                50                  55                  60

Phe Thr Leu Glu Ala Ile Ile Asp Ile Ser Ala Tyr Asn Glu Arg
                65                  70                  75

Thr Val Lys Gly Val Pro Ala Trp Leu Pro Leu Gly Ile Met Ser
                80                  85                  90

Asn Phe Glu Tyr Pro Leu Ala His Thr Val Ala Ala Leu Leu Thr
                95                  100                 105

Gly Ser Tyr Thr Ile Thr Gln Phe Thr His Asn Gly Gln Lys Phe
                110                 115                 120

Val Arg Val Asn Arg Leu Gly Thr Gly Ile Pro Ala His Pro Leu
                125                 130                 135

Arg Met Leu Arg Glu Gly Asn Gln Ala Phe Ile Gln Asn Met Val
                140                 145                 150

Ile Pro Arg Asn Phe Ser Thr Asn Gln Phe Thr Tyr Asn Leu Thr
                155                 160                 165

Asn Leu Val Leu Ser Val Gln Lys Leu Pro Asp Asp Ala Trp Arg
                170                 175                 180

Pro Ser Lys Asp Lys Leu Ile Gly Asn Thr Met His Pro Ala Val
                185                 190                 195

Ser Ile His Pro Asn Leu Pro Pro Ile Val Leu Pro Thr Val Lys
                200                 205                 210

Lys Gln Ala Tyr Arg Gln His Lys Asn Pro Asn Asn Gly Pro Leu
                215                 220                 225

Leu Ala Ile Ser Gly Ile Leu His Gln Leu Arg Val Glu Lys Val
                230                 235                 240

Pro Glu Lys Thr Ser Leu Phe Arg Ile Ser Leu Pro Ala Asp Met
                245                 250                 255

Phe Ser Val Lys Glu Gly Met Met Lys Lys Arg Gly Glu Asn Ser
                260                 265                 270

Pro Val Val Tyr Phe Gln Ala Pro Glu Asn Phe Pro Leu Asn Gly
                275                 280                 285

Phe Asn Asn Arg Gln Val Val Leu Ala Tyr Ala Asn Pro Thr Leu
                290                 295                 300

Ser Ala Val

<210> SEQ ID NO 5
<211> LENGTH: 329
<212> TYPE: PRT
<213> ORGANISM: Marburg Virus

<400> SEQUENCE: 5

Met Trp Asp Ser Ser Tyr Met Gln Gln Val Ser Glu Gly Leu Met
 1               5                  10                  15

Thr Gly Lys Val Pro Ile Asp Gln Val Phe Gly Ala Asn Pro Leu
                20                  25                  30
```

-continued

Glu Lys Leu Tyr Lys Arg Arg Lys Pro Lys Gly Thr Val Gly Leu
             35                  40                  45

Gln Cys Ser Pro Cys Leu Met Ser Lys Ala Thr Ser Thr Asp Asp
             50                  55                  60

Ile Ile Trp Asp Gln Leu Ile Val Lys Arg Thr Leu Ala Asp Leu
             65                  70                  75

Leu Ile Pro Ile Asn Arg Gln Ile Ser Asp Ile Gln Ser Thr Leu
             80                  85                  90

Ser Glu Val Thr Thr Arg Val His Glu Ile Glu Arg Gln Leu His
             95                 100                 105

Glu Ile Thr Pro Val Leu Lys Met Gly Arg Thr Leu Glu Ala Ile
            110                 115                 120

Ser Lys Gly Met Ser Glu Met Leu Ala Lys Tyr Asp His Leu Val
            125                 130                 135

Ile Ser Thr Gly Arg Thr Thr Ala Pro Ala Ala Ala Phe Asp Ala
            140                 145                 150

Tyr Leu Asn Glu His Gly Val Pro Pro Pro Gln Pro Ala Ile Phe
            155                 160                 165

Lys Asp Leu Gly Val Ala Gln Gln Ala Cys Ser Lys Gly Thr Met
            170                 175                 180

Val Lys Asn Ala Thr Thr Asp Ala Ala Asp Lys Met Ser Lys Val
            185                 190                 195

Leu Glu Leu Ser Glu Glu Thr Phe Ser Lys Pro Asn Leu Ser Ala
            200                 205                 210

Lys Asp Leu Ala Leu Leu Leu Phe Thr His Leu Pro Gly Asn Asn
            215                 220                 225

Thr Pro Phe His Ile Leu Ala Gln Val Leu Ser Lys Ile Ala Tyr
            230                 235                 240

Lys Ser Gly Lys Ser Gly Ala Phe Leu Asp Ala Phe His Gln Ile
            245                 250                 255

Leu Ser Glu Gly Glu Asn Ala Gln Ala Ala Leu Thr Arg Leu Ser
            260                 265                 270

Arg Thr Phe Asp Ala Phe Leu Gly Val Val Pro Pro Val Ile Arg
            275                 280                 285

Val Lys Asn Phe Gln Thr Val Pro Arg Pro Ser Gln Lys Ser Leu
            290                 295                 300

Arg Ala Val Pro Pro Asn Pro Thr Ile Asp Lys Gly Trp Val Cys
            305                 310                 315

Val Tyr Ser Ser Glu Gln Gly Glu Thr Arg Ala Leu Lys Ile
            320                 325

<210> SEQ ID NO 6
<211> LENGTH: 277
<212> TYPE: PRT
<213> ORGANISM: Marburg Virus

<400> SEQUENCE: 6

Met Gln Gln Pro Arg Gly Arg Ser Arg Thr Arg Asn His Gln Val
 1               5                  10                  15

Thr Pro Thr Ile Tyr His Glu Thr Gln Leu Pro Ser Lys Pro His
             20                  25                  30

Tyr Thr Asn Tyr His Pro Arg Ala Arg Ser Met Ser Ser Thr Arg
             35                  40                  45

Ser Ser Ala Glu Ser Ser Pro Thr Asn His Ile Pro Arg Ala Arg
             50                  55                  60

```
Pro Pro Ser Thr Phe Asn Leu Ser Lys Pro Pro Pro Lys
             65                  70                  75

Asp Met Cys Arg Asn Met Lys Ile Gly Leu Pro Cys Ala Asp Pro
         80                  85                  90

Thr Cys Asn Arg Asp His Asp Leu Asp Asn Leu Thr Asn Arg Glu
         95                 100                 105

Leu Leu Leu Leu Met Ala Arg Lys Met Leu Pro Asn Thr Asp Lys
            110                 115                 120

Thr Phe Arg Met Pro Gln Asp Cys Gly Ser Pro Ser Leu Ser Lys
            125                 130                 135

Gly Leu Ser Lys Asp Lys Gln Glu Gln Thr Lys Asp Val Leu Thr
            140                 145                 150

Leu Glu Asn Leu Gly His Ile Leu Ser Tyr Leu His Arg Ser Glu
            155                 160                 165

Ile Gly Asn Trp Met Arg His Leu Arg Ala Ala Leu Ser Leu Thr
            170                 175                 180

Cys Ala Gly Ile Arg Lys Thr Asn Arg Ser Leu Ile Asn Thr Met
            185                 190                 195

Thr Glu Leu His Met Asn His Glu Asn Leu Pro Gln Asp Gln Asp
            200                 205                 210

Gly Val Ile Lys Gln Thr Tyr Thr Gly Ile His Leu Asp Lys Gly
            215                 220                 225

Gly Gln Phe Glu Ala Ala Leu Trp Gln Gly Trp Asp Lys Arg Ser
            230                 235                 240

Ile Ser Leu Phe Val Gln Ala Ala Leu Tyr Val Met Asn Asn Ile
            245                 250                 255

Pro Cys Glu Ser Ser Ile Ser Val Gln Ala Ser Tyr Glu Ser Phe
            260                 265                 270

Tyr Ser Ser Ser Lys Ser Arg
            275

<210> SEQ ID NO 7
<211> LENGTH: 253
<212> TYPE: PRT
<213> ORGANISM: Marburg Virus

<400> SEQUENCE: 7

Met Ala Glu Leu Ser Thr Arg Tyr Asn Leu Pro Ala Asn Val Thr
 1               5                  10                  15

Glu Asn Ser Ile Asn Leu Asp Leu Asn Ser Thr Ala Arg Trp Ile
                20                  25                  30

Lys Glu Pro Ser Val Gly Gly Trp Thr Val Lys Trp Gly Asn Phe
                35                  40                  45

Val Phe His Ile Pro Asn Thr Gly Met Thr Leu Leu His His Leu
                50                  55                  60

Lys Ser Asn Phe Val Val Pro Glu Trp Gln Gln Thr Arg Asn Leu
                65                  70                  75

Phe Ser His Leu Phe Lys Asn Pro Lys Ser Thr Ile Ile Glu Pro
                80                  85                  90

Phe Leu Ala Leu Arg Ile Leu Leu Gly Val Ala Leu Lys Asp Gln
                95                 100                 105

Glu Leu Gln Gln Ser Leu Ile Pro Gly Phe Arg Ser Ile Val His
               110                 115                 120

Met Leu Ser Glu Trp Leu Leu Leu Glu Val Thr Ser Ala Ile His
               125                 130                 135
```

```
                        -continued

Ile Ser Pro Asn Leu Leu Gly Ile Tyr Leu Thr Ser Asp Met Phe
            140             145             150

Lys Ile Leu Met Ala Gly Val Lys Asn Phe Phe Asn Lys Met Phe
            155             160             165

Thr Leu His Val Val Asn Asp His Gly Lys Pro Ser Ser Ile Glu
            170             175             180

Ile Lys Leu Thr Gly Gln Gln Ile Ile Ile Thr Arg Val Asn Met
            185             190             195

Gly Phe Leu Val Glu Val Arg Arg Ile Asp Ile Glu Pro Cys Cys
            200             205             210

Gly Glu Thr Val Leu Ser Glu Ser Val Val Phe Gly Leu Val Ala
            215             220             225

Glu Ala Val Leu Arg Glu His Ser Gln Met Glu Lys Gly Gln Pro
            230             235             240

Leu Asn Leu Thr Gly Tyr Met Asn Ser Lys Ile Ala Ile
            245             250
```

METHODS FOR PRODUCING MARBURG VIRUS PROTEINS

This application is a divisional application of application Ser. No. 10/267,322, filed Oct. 9, 2002 now U.S. Pat. No. 7,090,852, which is a divisional application of U.S. Utility application Ser. No. 09/336,910, filed Jun. 21, 1999, now U.S. Patent No. 6,517,842, issued Feb. 11, 2003, which claims priority provisional application Ser. No. 60/091,403, filed Jun. 29, 1998.

Marburg virus (MBGV) was first recognized in 1967, when an outbreak of hemorrhagic fever in humans occurred in Germany and Yugoslavia, after the importation of infected monkeys from Uganda (Martini and Siegert, 1971, *Marburg Virus Disease*. Berlin: Springer-Verlag; Smith et al., 1982, Lancet 1, 816-820). Thirty-one cases of MBGV hemorrhagic fever were identified that resulted in seven deaths. The filamentous morphology of the virus was later recognized to be characteristic, not only of additional MBGV isolates, but also of Ebola virus (EBOV) (Johnson et al., 1977, *J. Virol.* 71, 3031-3038; Smith et al., 1982, Lancet 1, 816-820; Pattyn et al., 1977, Lancet 1, 573-574). MBGV and EBOV are now known to be distinctly different lineages in the family Filoviridae, within the viral order Mononegavirales (Kiley et al., 1982, *Intervirology* 18, 24-32; Feldmann and Klenk, 1996, *Adv. Virus Res.* 47, 1-52).

Few natural outbreaks of MBGV disease have been recognized, and all proved self-limiting, with no more than two cycles of human-to-human transmission. However, the actual risks posed by MBGV to global health cannot be assessed because factors which restrict the virus to its unidentified ecological niche in eastern Africa, and those that limit its transmissibility, remain unknown (Feldmann and Klenk, 1996, supra). Concern about MBGV is further heightened by its known stability and infectivity in aerosol form (Belanov et al., 1996, *Vopr. Virusol.* 41, 32-34; Frolov and Gusev Iu, 1996, *Vopr. Virusol.* 41, 275-277). Thus, laboratory research on MBGV is necessarily performed at the highest level of biocontainment. To minimize future risk, our primary interest has been the identification of appropriate antigens and vaccine strategies that can provide immunity to MBGV.

Early efforts to demonstrate the feasibility of vaccination against MBGV were only partially successful, as inoculation with formalin-inactivated viruses only protected about half the experimental animals (guinea pigs or nonhuman primates) from fatal disease (Ignat'ev. et al., 1991, *Vopr. Virusol.* 36, 421-423; Ignat'ev et al., 1996, *J. Biotechnol.* 44, 111-118). We recently demonstrated that the MBGV GP, cloned into a baculovirus vector and expressed as a soluble antigen to be administered in adjuvant, was sufficient to protect most but not all guinea pigs from lethal MBGV challenge (Hevey et al., 1997, *Virology* 239, 206-216). In addition, purified, $^{60}$Co-irradiated virus, administered in adjuvant, completely protected guinea pigs from challenge with either of two different strains of MBGV, thus setting a standard for future, more pragmatic, vaccine candidates (Hevey et al., 1997, supra). Experiences with EBOV vaccines have been similar to those with MBGV, reinforcing the difficulties of classical approaches (Lupton et al., 1980, *Lancet* 2, 1294-1295). Recent efforts to develop EBOV vaccines, using three distinctly different approaches (vaccinia recombinants, VEE replicon, and naked DNA) to achieve viral antigen expression in cells of vaccinated animals, showed that nucleoprotein (NP) as well as GP protected BALB/c mice (VanderZanden et al., 1998, *Virology* 245), whereas protection of guinea pigs by NP was unsuccessful (Gilligan et al., 1997, In: Brown, F., Burton, D., Doherty, P., Mekalanos, J., Norrby, E. (eds). 1997. *Vaccines* 97 Cold Spring Harbor Press. Cold Spring Harbor, N.Y.; Pushko et al., 1997, In: Brown, F., Burton, D., Doherty, P., Mekalanos, J., Norrby, E. (eds). 1997. *Vaccines* 97 Cold Spring Harbor Press. Cold Spring Harbor, N.Y.) or equivocal (Xu et al., 1998, Nat. Med. 4, 37-42).

Irrespective of how encouraging filovirus vaccine results may appear in guinea pigs or mice, protection of nonhuman primates is widely taken as the more definitive test of vaccine potential for humans. Low-passage viral isolates from fatal human cases of MBGV or EBOV tend to have uniform lethality in nonhuman primates, but not in guinea pigs or mice. Small animal models with fatal disease outcomes have been achieved only with a subset of filovirus isolates and only then by multiple serial passages in the desired host (Hevey et al., 1997, supra; Connolly et al., 1999, *J. Infect. Dis.* 179, suppl. 1, S203 ; Xu et al., 1998, supra; Bray et al., 1998, *J. Infect. Dis.* 178, 661-665). While highly useful for identification and initial characterization of vaccine candidates, guinea pig and murine models remain somewhat suspect with regard to the possibility that protection in such animals is easier to achieve than in nonhuman primates and, by inference, in humans. For example, with MBGV, peak viremias and viral titers in organs are more than 100 times higher in nonhuman primates than in guinea pigs.

Therefore, there is a need for an efficacious vaccine for MBGV useful for protecting humans against Marburg hemorrhagic fever.

SUMMARY OF THE INVENTION

The present invention satisfies the need discussed above. The present invention relates to a method and composition for use in inducing an immune response which is protective against infection with MBGV.

In this study a vaccine delivery system based on a Venezuelan equine encephalitis (VEE) virus replicon was used to identify candidate protective antigens in nonhuman primates. In this vaccine strategy, a gene coding for a protein of interest is cloned in place of the VEE virus structural genes; the result is a self-replicating RNA molecule that encodes its own replicase and transcriptase functions, and in addition makes abundant quantities of mRNA encoding the foreign protein. When replicon RNA is transfected into eukaryotic cells along with two helper RNAs that express the VEE structural proteins (glycoproteins and nucleocapsid), the replicon RNA is packaged into VEE virus-like particles by the VEE virus structural proteins, which are provided in trans. Since the helper RNAs lack packaging signals neccessary for further propagation, the resulting VEE replicon particles (VRPs) which are produced are infectious for one cycle but are defective thereafter. Upon infection of an individual cell with a VRP, an abortive infection occurs in which the infected cell produces the protein of interest in abundance, is ultimately killed by the infection, but does not produce any viral progeny (Pushko et al., 1997, *Virology* 239, 389-401). The VEE replicon is described in greater detail in U.S. Pat. No. 5,792,462 issued to Johnston et al. on Aug. 11, 1998.

Results shown here demonstrate that the VEE replicon is a potent tool for vaccination with MBGV antigens. Guinea pigs were protected by vaccination with packaged replicons that expressed GP, or by either of two replicons which expressed internal MBGV antigens (NP and VP35). GP expressed from the VEE replicon elicited an even more robust immunity than was achieved previously with a baculovirus-produced soluble GP administered in adjuvant. When results were extended to nonhuman primates, complete protection with GP was demonstrated. The data shown here constitute the most emphatic proof to date that an efficacious vaccine for MBGV is feasible, and define candidate antigens for such a vaccine.

Therefore, it is one object of the present invention to provide a VEE virus replicon vector comprising a VEE virus replicon and a DNA fragment encoding any of the MBGV GP, NP, VP40, VP35, VP30, and VP24, and GPΔTM, a GP deletion mutant from which the C-terminal 39 amino acids encoding the transmembrane region and cytoplasmic tail of MBGV GP were removed.

It is another object of the present invention to provide a self replicating RNA comprising the VEE virus replicon and any of the MBGV GP, GPΔTM, NP, VP40, VP35, VP30, and VP24 described above.

It is another object of the present invention to provide infectious VEE virus replicon particles produced from the VEE virus replicon RNA described above.

It is further an object of the invention to provide an immunological composition for the protection of mammals against MBGV infection comprising VEE virus replicon particles containing nucleic acids encoding any of the MBGV GP, GPΔTM, NP, VP40, VP35, VP30, and VP24 or a combination of different VEE virus replicons each containing nucleic acids encoding a different MBGV protein from any of MBGV GP, GPΔTM, NP, VP40, VP35, VP30, and VP24.

BRIEF DESCRIPTION OF THE DRAWINGS

These and other features, aspects, and advantages of the present invention will become better understood with reference to the following description and appended claims, and accompanying drawings where:

FIG. 1 Indirect immunofluorescence of Vero cells infected with packaged VEE replicons expressing the indicated antigens.

Figure 6:
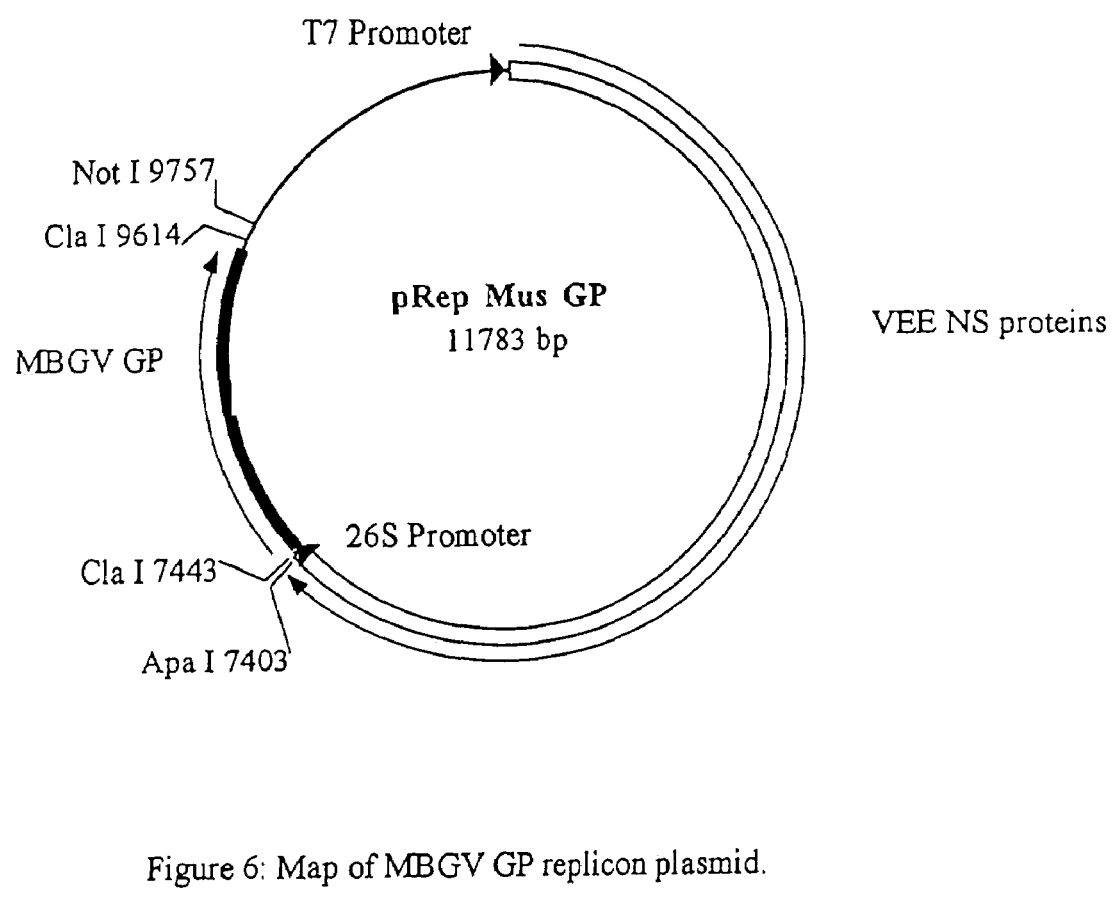
Figure 7:
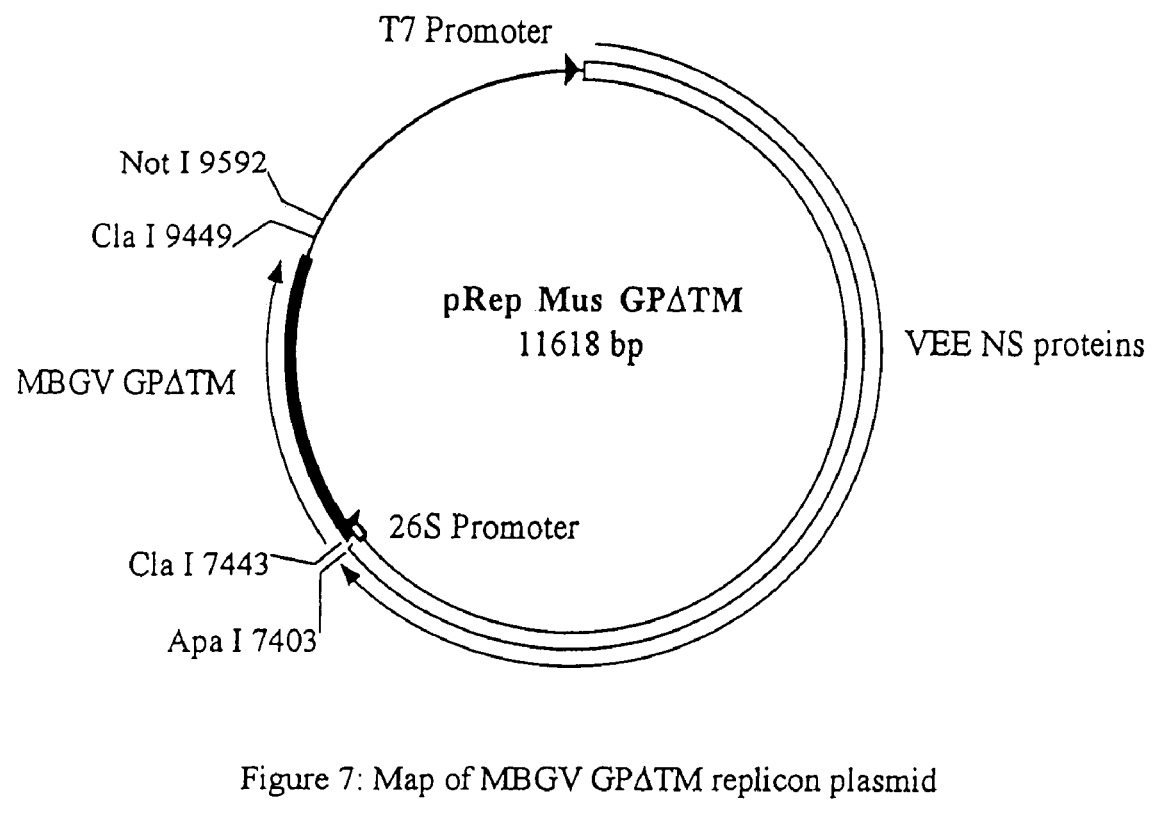

FIG. 6: Schematic of pRep Mus GP.
FIG. 7: Schematic of pRep Mus GPΔTM.
FIG. 8: Schematic of pRep Mus NP.
FIG. 9: Schematic of pRep Mus VP40.
FIG. 10: Schematic of pRep Mus VP35.
FIG. 11: Schematic of pRep Mus VP30.
FIG. 12: Schematic of pRep Mus VP24.

DETAILED DESCRIPTION

Figure 2:
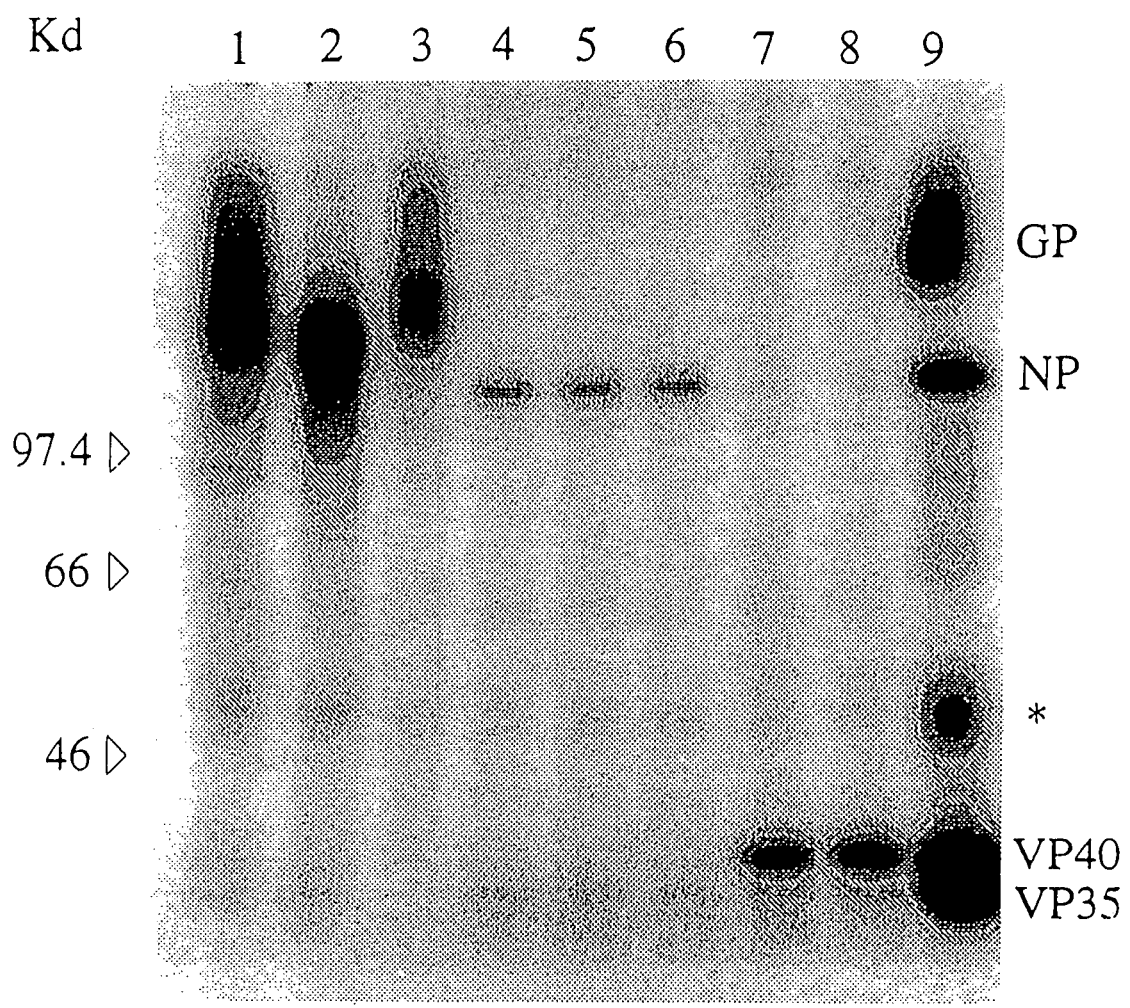
FIG. 2 Immunoprecipitation of MBGV proteins expressed from an alphavirus replicon in Vero cells using convalescent guinea pig polyclonal anti-MBGV serum. Lane 1, cell lysate from Vero cells infected with MBGV GP replicon; lane 2, cell lysate from Vero cells infected with MBGV GPΔTM replicon; lane 3, supernatant from Vero cells infected with MBGV GPΔTM replicon; lanes 4-6, cell lysate from Vero cells infected with various clones of MBGV NP replicon; lanes 7-8, cell lysate from Vero cells infected with various clones of MBGV VP40 replicon; lane 9, sucrose gradient-purified $^{35}$S-labeled MBGV, * an unidentified 46-50 KDa protein observed in virion preparations.

In the description that follows, a number of terms used in recombinant DNA, virology and immunology are extensively utilized. In order to provide a clearer and consistent understanding of the specification and claims, including the scope to be given such terms, the following definitions are provided.

Filoviruses. The filoviruses (e.g. Marburg virus, MBGV) cause acute hemorrhagic fever characterized by high mortality. Humans can contract filoviruses by infection in endemic regions, by contact with imported primates, and by performing scientific research with the virus. However, there currently are no available vaccines or effective therapeutic treatments for filovirus infection. The virions of filoviruses contain seven proteins which include a surface glycoprotein (GP), a nucleoprotein (NP), an RNA-dependent RNA polymerase (L), and four virion structural proteins (VP24, VP30, VP35, and VP40). Little is known about the biological functions of these proteins and it is not known which antigens significantly contribute to protection and should therefore be used to induce an immune response by an eventual vaccine candidate.

Replicon. A replicon is equivalent to a full length virus from which all of the viral structural proteins have been deleted. A multiple cloning site can be cloned into the site previously occupied by the structural protein genes. Virtually any heterologous gene may be cloned into this cloning site. Transcription of the RNA from the replicon yields an RNA capable of initiating infection of the cell identical to that seen with the full-length infectious virus clone. However, in lieu of the viral structural proteins, the heterologous antigen is expressed. This system does not yield any progeny virus particles because there are no viral structural proteins available to package the RNA into particles.

Particles which appear structurally identical to virus particles can be produced by supplying structural proteins for packaging of the replicon RNA in trans. This is typically done with two helpers also called defective helper RNAs. One helper consists of a full length infectious clone from which the nonstructural protein genes and the glycoprotein genes are deleted. The helper retains only the terminal nucleotide sequences, the promoter for subgenomic mRNA transcription and the sequences for the viral nucleocapsid protein. The second helper is identical to the first except that the nucleocapsid gene is deleted and only the glycoprotein genes are retained. The helper RNA's are transcribed in vitro and co-transfected with replicon RNA. Because the replicon RNA retains the sequences for packaging by the nucleocapsid protein, and because the helpers lack these sequences, only the replicon RNA is packaged by the viral structural proteins and released from the cell. The particles can then by inoculated into animals similar to parent virus. The replicon particles will initiate only a single round of replication because the helpers are absent, they produce no progeny virus particles, and express only the viral nostructural proteins and the product of the heterologous gene cloned in place to the structural proteins.

The VEE virus replicon is a genetically reorganized version of the VEE virus genome in which the structural proteins genes are replaced with a gene from an immunogen of interest, in this invention, the MBGV virion proteins. The result is a self replicating RNA (replicon) that can be packaged into infectious particles using defective helper RNAs that encode the glycoprotein and capsid proteins of the VEE virus.

Subject. Includes both human, animal, e.g., horse, donkey, pig, guinea pig, mouse, hamster, monkey, chicken, bats, birds and insects such as mosquito.

In one embodiment, the present invention relates to a recombinant DNA molecule that includes a VEE replicon and a DNA sequence encoding any of MBGV virion proteins GP, GPΔTM, NP, VP40, VP35, VP30, VP24. The sequences encoding the Marburg proteins GP, GPΔTM, NP, VP40, VP35, VP30, VP24 corresponding to nucleotides 104-11242 of the Genbank sequence is presented in SEQ ID NO:1; the GP DNA fragment extends from nucleotide 5932 to 8033, of which nucleotides 5940-7985 encode the protein identified in SEQ ID NO:2; the GPΔTM DNA fragment, a GP deletion mutant from which the C-terminal 39 amino acids encoding the transmembrane region and cytoplasmic tail of MBGV GP were removed, extends from nucleotides 5933 to 7869, of which nucleotides 5940-7871 encode the protein; NP, identified in SEQ ID NO:3, is encoded by the DNA fragment extending from nucleotides 104 to 2195; VP40 DNA fragment extends from nucleotide 4564 to 5958, of which nucleotides 4567-5416 encode the protein identified in SEQ ID NO:4; VP35 DNA fragment extends from nucleotide 2938 to 4336, of which nucleotides 2944-3933 encode the protein identified in SEQ ID NO:5; VP30 DNA fragment extends from nucleotide 8861 to 9979, of which nucleotides 8864-9697 encode the protein identified in SEQ ID NO:6; VP24 DNA fragment extends from nucleotide 10182 to 11242, of which nucleotides 10200-10961 encode the protein identified in SEQ ID NO:7.

When the DNA sequences described above are in a replicon expression system, such as the VEE replicon described above, the proteins can be expressed in vivo. The DNA sequence for any of the MBGV virion proteins described above can be cloned into the multiple cloning site of a replicon such that transcription of the RNA from the replicon yields an infectious RNA containing the sequence(s) which encodes the MBGV virion protein or proteins of interest. Use of helper RNA containing sequences necessary for encapsulation of the viral transcript will result in the production of viral particles containing replicon RNA which are able to infect a host and initiate a single round of replication resulting in the expression of the MBGV virion proteins. Such replicon constructs include, for example, VP24 cloned into a VEE replicon, pRep Mus VP24, VP30 cloned into a VEE replicon, pRep Mus VP30, VP35 cloned into a VEE replicon, pRep Mus VP35, and VP40 cloned into a VEE replicon, pRep Mus VP40, NP cloned into a VEE replicon, pRep Mus NP, GP cloned into a VEE replicon, pRep Mus GP, GPΔTM cloned into a VEE replicon, pRep Mus GPΔTM. The sequences encoding the MBGV proteins were cloned into the replicon vector by methods known in the art and described below in Materials and Methods. Schematic diagrams of the resulting constructs are shown in the Figures. The VEE constructs containing Marburg proteins can be used as a DNA vaccine, or for the production of RNA molecules as described below.

In another embodiment, the present invention relates to RNA molecules resulting from the transcription of the constructs described above. The RNA molecules can be prepared by in vitro transcription using methods known in the art and described in the Examples below. Alternatively, the RNA molecules can be produced by transcription of the constructs in vivo, and isolating the RNA. These and other methods for obtaining RNA transcripts of the constructs are known in the art. Please see Current *Protocols in Molecular Biology*. Frederick M. Ausubel et al. (eds.), John Wiley and Sons, Inc. The RNA molecules can be used, for example, as a direct RNA vaccine, or to transfect cells along with RNA from helper plasmids, one of which expresses VEE glycoproteins and the other VEE capsid proteins, as described above, in order to obtain replicon particles.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to mouse and human). Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with, prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Please see e.g., Maniatis, Fitsch and Sambrook, *Molecular Cloning; A Laboratory* Manual (1982) or *DNA Cloning*, Volumes I and II (D. N. Glover ed. 1985) for general cloning methods. The DNA sequence can be present in the vector operably linked to a sequence encoding an IgG molecule, an adjuvant, a carrier, or an agent for aid in purification of MBGV virion proteins, such as glutathione S-transferase. The recombinant molecule can be suitable for transfecting eukaryotic cells, for example, mammalian cells and yeast cells in culture systems. *Saccharomyces cerevisiae, Saccharomyces carlsbergensis*, and *Pichia pastoris* are the most commonly used yeast hosts, and are convenient fungal hosts. Control sequences for yeast vectors are known in the art. Mammalian cell lines available as hosts for expression are known in the art and include many immortalized cell lines available from the American Type Culture Collection (ATCC), such as CHO cells, vero cells, and COS cells to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences and poly A addition sequences; enhancer sequences which increase expression may also be included, and sequences which cause amplification of the gene may also be desirable. These sequences are known in the art.

The transformed or transfected host cells can be used as a source of DNA sequences described above. When the recombinant molecule takes the form of an expression system, the transformed or transfected cells can be used as a source of the protein cloned into the VEE replicon, or a source of RNA transcribed from the replicon as described above, or a source of replicon particles.

In a further embodiment, the present invention relates to a method of producing the recombinant or fusion protein which includes culturing the above-described host cells, under conditions such that the DNA fragment is expressed and the recombinant or fusion protein is produced thereby. The recombinant or fusion protein can then be isolated using methodology well known in the art. The recombinant or fusion protein can be used as a vaccine for immunity against infection with MBGV or as a diagnostic tool for detection of MBGV infection. The transformed host cells can be used to analyze the effectiveness of drugs and agents which inhibit MBGV virus function, such as host proteins or chemically derived agents or other proteins which may interact with the virus to inhibit its replication or survival.

In another embodiment, the present invention relates to a MBGV vaccine comprising one or more replicon particles derived from one or more replicons encoding one or more MBGV virion proteins. The present invention relates to a method for providing immunity against MBGV virus said method comprising administering one or more replicon particles containing any combination of the MBGV virion proteins to a subject such that a protective immune reaction is generated. Even though the MBGV strain Musoke was used in the examples below, it is expected that protection would be afforded using virion proteins from other MBGV strains, as well as significant cross protection between strains.

Vaccine formulations of the present invention comprise an immunogenic amount of a replicon particle, resulting from one of the replicon constructs described above, or a combination of replicon particles as a multivalent vaccine, in combination with a pharmaceutically acceptable carrier. An "immunogenic amount" is an amount of the replicon particles sufficient to evoke an immune response in the subject to which the vaccine is administered. An amount of from about $10^5$ to $10^8$ or more replicon particles per dose with one to three doses one month apart is suitable, depending upon the age and species of the subject being treated. Exemplary pharmaceutically acceptable carriers include, but are not limited to, sterile pyrogen-free water and sterile pyrogen-free physiological saline solution.

Administration of the replicon particles disclosed herein may be carried out by any suitable means, including both parenteral injection (such as intraperitoneal, subcutaneous, or intramuscular injection), by in ovo injection in birds, orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed.

When the replicon RNA or DNA is used as a vaccine, the replicon RNA or DNA can be administered directly using techniques such as delivery on gold beads (gene gun), delivery by liposomes, or direct injection, among other methods known to people in the art. Any one or more constructs or replicating RNA described above can be use in any combination effective to illicit an immunogenic response in a subject. Generally, the nucleic acid vaccine administered may be in an amount of about 1-5 ug of nucleic acid per dose and will depend on the subject to be treated, capacity-of the subject's immune system to develop the desired immune response, and the degree of protection desired. Precise amounts of the vaccine to be administered may depend on the judgement of the practitioner and may be peculiar to each subject and antigen.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

The following MATERIALS AND METHODS were used in the examples that follow.

Cell Cultures and Viruses

Vero E6 (Vero C1008, ATCC CRL 1586), Vero 76 (ATCC CRL 1587), and BHK (ATCC CCL 10) cells were grown in minimal essential medium with Earle's salts supplemented with 10% fetal bovine serum and gentamicin (50 μg/ml). MBGV (strain Musoke) was isolated from a human case in 1980 in Kenya (Smith et al., 1982, Lancet 1, 816-820), and a derivative of this virus (six passages in Vero 76 cells) was used to challenge the cynomolgus monkeys. The MBGV (Musoke) that was adapted for guinea pig lethality and plaque-picked three times was described previously (Hevey et al., 1997, Virology 239, 206-210).

Construction of Recombinant VEE Replicons

MBGV gene clones pGem-GP, pGem-NP, pTM1-VP40, pTM1-VP35, pTM1-VP30, and pTM1-VP24 were generously provided by Heinz Feldmann and Anthony Sanchez (Centers for Disease Control and Prevention, Atlanta, Ga.) (Will et al., 1993, J. Virol. 67, 1203-1210; Sanchez et al., 1992, J. Gen. Virol. 73, 347-357; Feldman et al., 1992, Virus Res. 24, 1-19). VEE replicon and shuttle vector as well as the replicons that express Lassa virus NP and Flu HA were previously described (Pushko et al., 1997, *Virology* 239, 289-401). The MBGV GP gene from pGem-GP was excised with Sal I and subcloned into the Sal I site of the shuttle vector by using standard techniques (Sambrook et al., 1989, *Molecular Cloning: A Laboratory Manual.* 2 ed. Cold Spring Harbor Laboratory Press, Cold Spring Harbor). A clone with the MBGV GP gene in the correct orientation was excised with Apa I and Not I and this fragment was cloned into the Apa I and Not I sites of the VEE replicon plasmid.

Construction of pBluescript-KS(+)-GPΔTM, a deletion mutant of MBGV from which the C-terminal 39 amino acids (transmembrane region and cytoplasmic tail) of MBGV GP were removed, was previously described (Hevey et al., 1997, supra). Here, the MBGV GPΔTM gene was excised from pBluescript-KS(+) with Hind III, and the resulting fragment ligated into the Hind III site of the shuttle vector. MBGV GPΔTM gene was excised from the shuttle vector using-Cla I, and the resulting fragment ligated into the VEE replicon plasmid.

The MBGV NP gene was amplified by PCR performed with 1 ng of pGem NP as template DNA, 1 µg each of forward (5'-CCG ACC ATG GAT TTA CAC AGT TTG TTG G-3', SEQ ID NO:8) and reverse primer (5'-CTA GCC ATG GCT GGA CTA CAA GTT CAT CGC-3' SEQ ID NO:9), and AmpliTaq polymerase (GeneAmp PCR reagent kit, Perkin Elmer, Branchburg, N.J.). The primers contained an NcoI recognition sequence at the 3' terminus end (5-10 inclusive for both the forward and reverse primers). The reaction conditions were: 40 cycles of 94° C. for 45 sec, 50° C. for 45 sec, and 72° C. for 1 min., followed by a final extension step at 72° C. for 5 min. The product was cloned into the pCR™II (InVitrogen, Carlsbad, Calif.) vector, excized with Eco RI, then subcloned into the shuttle vector using Eco RI sites. The MBGV NP gene was excised with Cla I and ligated into the VEE replicon plasmid.

The MBGV VP40, VP35, VP30, and VP24 genes were excised from pTM1 with Bam HI and ligated into the Bam HI site of the shuttle vector. These MBGV genes were then excised from shuttle vectors using either Cla I (VP35, VP30, and VP24) or Apa I and Not I (VP40) and ligated into the VEE replicon plasmid.

Packaging of Replicons into VEE-Like Particles and Determination of Replicon Titer Replicon RNAs were packaged into VRPs as described previously (Pushko et al., 1997, *Virology* 239, 389-401). Briefly, BHK cells were cotransfected with RNA transcribed in vitro from the replicon plasmid and from two helper plasmids, one of which expressed VEE glycoproteins and the other VEE capsid protein. The cell culture supernatant was harvested approximately 30 h after transfection and the replicon particles were concentrated and partially purified by pelleting through a 20% sucrose cushion (SW28 rotor, 25,000 rpm, 4 h), after which they were resuspending in 1 ml PBS. To assay titers of packaged replicons, Vero cells ($10^5$ cells per well in eight-chamber slides, Labtek slides, Nunc Inc.) were infected with serial dilutions of the replicon particles and incubated for 16-18 h at 37° C. to allow for expression of the MBGV genes. After rinsing and fixating with acetone, antigen-positive cells were identified by indirect immunofluorescence assay (IFA) as described previously (Schmaljohn et al, 1995, *Virology* 206, 963-972). The antibodies used included MAbs specific for MBGV GP (II-7C11), NP (III-5F8), VP40 (III-1H11), VP35 (XBC04-BG06), and VP30 (III-5F11 and 5F12) (Hevey et al., 1997, supra). To detect VP24 antigen, a monkey anti-MBGV serum was used, a monkey anti-Lassa serum was used to detect expression of Lassa NP in cells, and influenza HA was detected with serum from a mouse immunized with a VEE replicon expressing influenza HA (provided by Dr. Mary Kate Hart, USAMRIID).

Immunoprecipitation and Gel Electrophoresis of Proteins Expressed by VEE Replicons Expressed MBGV antigens were immunoprecipitated and analyzed by gel electrophoresis as described previously (Hevey et al., 1997, supra). Briefly, Vero cells were infected (MOI≧23) with VRP expressing a single MBGV antigen. Complete medium was replaced 16-18 h postinfection by methionine- and cysteine-free medium for 1 h, and monolayers were then labeled with $^{35}S$-methionine and cysteine for 4 h. Convalescent guinea pig anti-MBGV (group 1, Table 5, in Hevey et al., 1997, supra) was used to immunoprecipitate MBGV-specific proteins from the resulting cell lysates.

Vaccination of Guinea Pigs with VEE Replicons Expressing MBGV Proteins

Inbred strain 13 guinea pigs (maintained as a colony at USAMRIID) were inoculated subcutaneously with $10^6$ focus-forming units (FFU) of VRP in a total volume of 0.5 ml administered at two dorsal sites. Guinea pigs were anesthetized, bled, and those that received two or three doses of replicon inoculated (as described for the first vaccine dose) 28 days after the primary vaccination. Guinea pigs were anesthetized and bled again 28 days later, and animals that received three doses of replicons were inoculated, as described above. Animals were anesthetized and bled 21 days later, and challenged 7 days after the last bleed with $10^{3.0}$ plaque forming units (PFU) (ca. 2000 $LD_{50}$) guinea pig adapted MBGV. Animals were examined daily for signs of illness. Heparinized plasma was obtained from the retroorbital sinus of anesthetized animals 7 days postinfection for assay of viremia. Surviving guinea pigs were observed for at least 30 days after challenge, then anesthetized and exsanguinated. Viremia titers was measured by plaque assay on Vero E6 cells.

Vaccination of Cynomolgus Monkeys with Replicons

Twelve cynomolgus macaques (*Macaca fascicularis*), 11 females and 1 male, ranging from 2.8 to 4.5 Kg, were inoculated subcutaneously with $10^7$ FFU of VRP in a total volume of 0.5 ml at one site. Monkeys were anesthetized with ketamine, bled, and inoculated (as described for the first vaccine dose) 28 days after the primary injection, and again 28 days after the second. Animals were anesthetized and bled 21 days after the third vaccine dose, then were challenged 14 days later with $10^{3.9}$ PFU MBGV subcutaneously. Here and in guinea pig experiments, the inoculum was back-titrated to ensure proper dose delivery. Animals were examined daily by the attending veterinarian for signs of illness, and given buprenorphine (Buprenex) at a dosage of 0.01 mg/kg body weight, to provide-analgesia upon signs of distress. Of the unprotected animals, three succumbed abruptly, while one was euthanized in extremis. A detailed clinical evaluation, serum for viremia determination and blood chemistries, as well as EDTA blood was obtained from anesthetized animals 17 days before and 3, 5, 7, 10, 17, and 32 days postinfection. Viremia was measured by plaque assay on Vero E6 cells.

MBGV ELISA and Infectivity Assays

Antibody titers in guinea pig plasmas or monkey sera were determined by an indirect ELISA as described previously (Hevey et al., 1997, supra). Briefly, antigen consisting of purified, irradiated virus was coated directly onto PVC plates and serial dilutions of test serum were added to wells containing antigen. The presence of bound antibody was detected by use of the appropriate horseradish peroxidase conjugated anti-species antibody (HPO-goat-anti-guinea pig IgG H+L; HPO-goat-anti-monkey IgG H+L). Endpoint of reactivity was defined as the dilution at which $OD_{405}$ was 0.2 as determined by extrapolation of a four parameter curve fit (SOFTmax®, Molecular Devices Corp. Sunnydale, Calif.) of background-subtracted mean OD versus dilution. Results shown in any table or figure are from a single assay to allow more valid comparison of endpoints. Plaque assays were performed on Vero E6 cells with a semi-solid overlay on serial dilutions of samples. Viral plaques were visualized by staining viable cells with neutral red 6-7 days postinfection. To measure plaque reduction neutralization, equal volumes of a virus stock (target plaque dose was 100 PFU) and serum diluted in cell culture medium were mixed and incubated at 37° C. for 1 h. The resulting sample was assayed by plaque assay on Vero E6 cells for more than a 50% reduction in PFU compared to control samples.

Clinical Laboratory Assays

For nonhuman primate studies, hematological results were obtained with a Coulter instrument, and differential counts were performed manually. Clinical chemistry results were obtained with a Piccolo™ analyzer (Abaxis, Inc., Sunnydale, Calif.) using the diagnostic panel General Chemistry 12, which measures alanine aminotransferase (ALT), albumin, alkaline phosphatase (ALP), amylase, aspartate aminotransferase (AST), calcium, cholesterol, creatinine, glucose, total bilirubin, total protein, and urea nitrogen.

EXAMPLE 1

Figure 1:
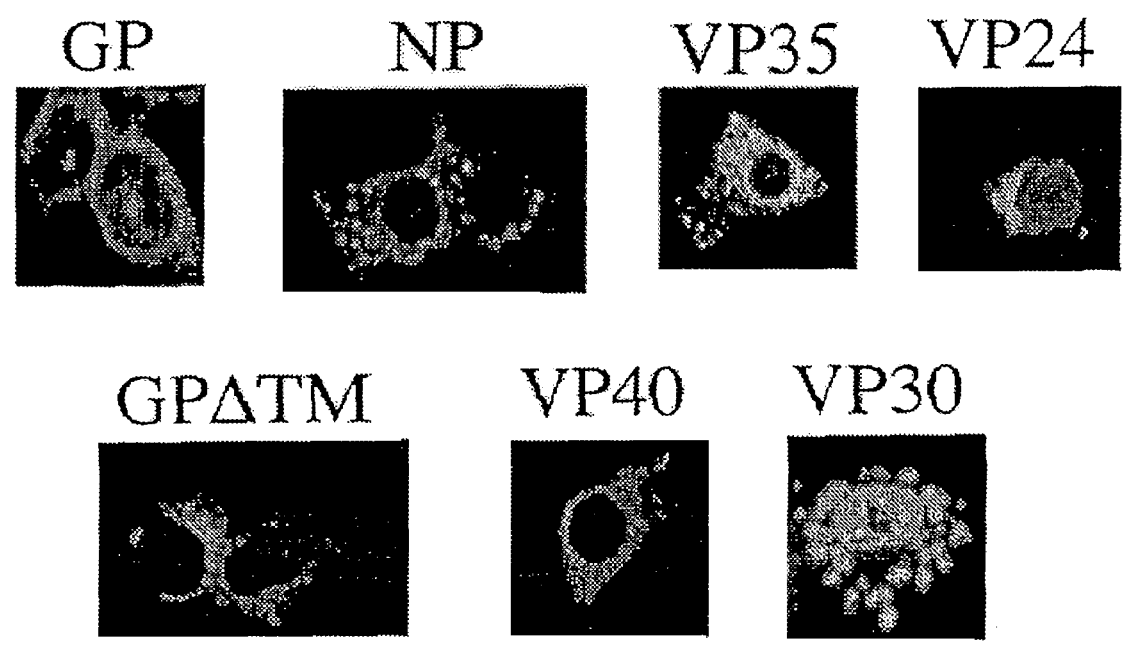

Analysis of Protein Products Synthesized After Infection of Vero Cells with VEE Replicons that Expressed MBGV Proteins Results of indirect immunofluorescence assay (IFA) analyses of Vero cells infected with different recombinant VEE replicons expressing MBGV proteins, are shown in FIG. 1. Expression of the indicated protein products was detected both with polyclonal guinea pig anti-MBGV and with monoclonal antibodies (MAbs) specific for the indicated MBGV proteins or, in the case of VP24 (for which no MAbs were available), with convalescent serum from a monkey that had survived infection with MBGV. There were distinct staining patterns for several of the expressed proteins. MBGV GP was observed as a plasma membrane fluorescence, while the GPΔTM provided a more diffuse cytoplasmic staining. These different staining patterns were not unexpected as GPΔTM, which lacks the hydrophobic transmembrane region of GP, is a secreted product. MBGV NP and VP35 formed discrete patterns in the cytoplasm of cells. MBGV VP40 demonstrated a more diffuse cytoplasmic staining pattern. MBGV VP30 was present in unique large globules staining in the cytoplasm of cells. MBGV VP24 staining was typically perinuclear. In summary, IFA served to assure that the appropriate antigen was expressed in a given preparation; it highlighted staining patterns, which demonstrated the localization of the expressed MBGV proteins in Vero cells; and it served as the basis for the assay whereby 10-fold dilutions of VRPs were quantitated for infectivity, as focus forming units (FFU)

Expression, antigenicity, and size determination of the MBGV proteins were confirmed by immunoprecipitation and gel electrophoresis. The results obtained from expression of MBGV GP, GPΔTM, NP, and VP40 in Vero cells are shown in FIG. 2. Products of the expected sizes were specifically immunoprecipitated from replicon-infected cell lysates. Glycosylation of MBGV GP more than doubles the predicted size of the peptide chain, and typically results in a heterogeneous array of posttranslationally modified products (Feldmann et al., 1991, *Virology* 182, 353-356; Feldman et al., 1994, *Virology* 199, 469-473), especially in GP from cell lysates, as shown in FIG. 2, lane 1. As expected and shown previously in the baculovirus system, GPΔTM was secreted, and thus present in the supernatant of replicon-infected cells (FIG. 2, Lane 3). Appropriately, both the cell-associated (lane 2) and-secreted (lane 3) forms of GPΔTM appeared smaller than the largest forms of GP (lane 1). The secreted form of GPΔTM appeared larger and somewhat more homogeneous than the same molecule from cell lysates, as noted previously (Hevey et al., 1997, supra) (compare FIG. 2, Lanes 2 and 3). This difference likely reflects the more complete glycosylation of the secreted product compared to partially glycosylated forms of this protein expected to be present in the cell. In this gel, and with considerably less intensity in other preparations, an unidentified protein of approximately 46 KDa, which can be immunoprecipitated with GP-specific monoclonal antibodies (not shown), is evident in MBGV virions (FIG. 2, Lane 9). Although it remains to be confirmed, this product may be the glycosylated form of a putative 27 KDa cleavage product of GP, reported to be the result of a posttranslational, furin-mediated cleavage of GP (Volchkov et al, 1998, *Proc. Natl. Acad. Sci. USA* 95:5762-5767). Replicon-expressed MBGV NP ( FIG. 2, Lanes 4-6) and VP40 (FIG. 2, Lanes 7-8) comigrated with the authentic proteins present in purified MBGV virions. In other experiments, the reactivity with polyclonal or MAbs and the authentic electrophoretic migrations of the remaining replicon-expressed MBGV proteins (VP30, VP35, and VP24) were similarly demonstrated (data not shown).

EXAMPLE 2

Protective Efficacy of VEE Replicons Expressing MBGV Proteins in Strain 13 Guinea Pigs Groups of strain 13 guinea pigs were inoculated with packaged recombinant VEE replicons expressing individual MBGV proteins, and later challenged with $10^{3.3}$ $LD_{50}$ guinea pig-adapted MBGV subcutaneously. Results are shown in Table 1. MBGV GP protected guinea pigs from both death and viremia when administered as a three dose regimen. In addition, no reduction in efficacy or potency was observed when a two dose regimen was instituted, and significant efficacy was observed even when a single dose of $10^6$ FFU of VRP expressing MBGV GP was used as an immunogen. The efficacy of either the two or three dose vaccine schedule was further demonstrated by the observation that no boost in postchallenge ELISA titers were observed. This result suggested minimal antigen exposure after challenge with MBGV, and thus robust or even sterile immunity in these animals. MBGV GPΔTM, which was previously shown to be protective as a vaccine when produced from insect cells, also protected guinea pigs from death and viremia when delivered in an VEE virus replicon. Again, there were no increases in postchallenge ELISA titers in the group of animals immunized with GPΔTM, thus no differences were discerned in the vaccine efficacy of membrane-bound versus soluble GP.

TABLE 1

Protection of replicon inoculated strain 13 guinea pigs from lethal challenge with Marburg virus (Musoke isolate)

| Antigen | # of Doses Replicon | S/T[a] | Log 10 ELISA Titer* | | Viremia[b] | V/T[c] | MDD |
|---|---|---|---|---|---|---|---|
| | | | Day-7 | Day 64 | | | |
| GP | 3 | 6/6** | 4.21 | 3.80 | <1.7 | 0/6 | — |
| GP | 2 | 6/7** | 4.30 | 4.06 | <1.7 | 0/6 | — |
| GP | 1 | 5/6* | 2.89 | 4.19 | 4.1 | 1/6 | 9 |
| NP | 3 | 6/6** | 3.38 | 3.94 | <1.7 | 0/6 | — |
| VP40 | 3 | 1/6 | 2.83 | 2.68 | 4.5 | 5/6 | 10 |
| GPΔTM | 3 | 6/6** | 3.93 | 3.65 | <1.7 | 0/6 | — |
| VP35 | 3 | 5/6* | 1.99 | 3.75 | 3.7 | 5/6 | 13 |
| VP30 | 3 | 0/6 | 2.23 | — | 5.8 | 6/6 | 10 |
| VP24 | 3 | 1/6 | <1.5 | 4.31 | 5.6 | 6/6 | 11 |
| Lassa NP | 3 | 1/6 | <1.5 | 4.19 | 6.0 | 5/6 | 10 |
| None | — | 1/6 | <1.5 | 4.25 | 5.2 | 5/6 | 11 |

*Endpoint titer of equal volumes of serum pooled from animals in each group against MBGV Musoke
[a]Survivors/Total (S/T) on day 30 postinfection.
**indicates p < 0.01,
*indicates p < 0.05.
[b]Viremia ($Log_{10}$ PFU/ml) day 7 postinfection. Where ≧2 animals were viremic, a GMT was calculated.
[c]Viremic animals/total (V/T) on day 7 postinfection. All animals that died were viremic.

In the experiment shown, MBGV NP protected all vaccinated guinea pigs from both viremia and death, while MBGV VP35 vaccination resulted in five of six animals surviving, but four of the five survivors were viremic seven days postinfection. None of the other MBGV viral proteins cloned into VEE replicons evoked significant protection against a lethal challenge with MBGV. Thus, the proteins that showed the most promise as vaccine candidates in the guinea pig model were MBGV GP and NP. Cumulative results from this and additional experiments (not shown) in strain 13 guinea pigs inoculated three times with VRPs demonstrated complete survival with GP (18/18), and less complete protection with NP (16/18) and VP35 (13/18) as compared with controls (2/24).

EXAMPLE 3

Protection of Cynomolgus Monkeys Vaccinated with Recombinant VEE Replicons Expressing Either MBGV GP and/or NP Encouraged by the success in vaccinating guinea pigs against MBGV, we evaluated the ability of these same VEE replicons to protect cynomolgus macaques from lethal MBGV infection. The monkeys received 10-fold higher doses of replicons, but on an identical schedule as tested in the guinea pigs. Four groups contained three monkeys each. One group received VRPs which expressed MBGV GP; a second group received VRPs which expressed MBGV NP; a third group received a mixture of MBGV GP and MBGV NP VRPs; and a fourth received VRPs which expressed a control antigen (influenza HA) irrelevant to MBGV immunity. Anti-MBGV ELISA antibody titers were monitored throughout the experiment.

All animals that received VEE replicons expressing MBGV GP, either alone or in combination with MBGV NP, survived challenge with 8000 PFU MBGV without any observed signs of illness (Table 2). Of the three animals vaccinated with MBGV NP, one died 8 days after challenge from MBGV disease. The other two NP recipients displayed signs of illness 7-9 days after challenge, but eventually recovered. One NP-inoculated survivor had a relatively mild disease (slightly reduced activity and responsiveness), while the other had severe disease which included obvious petechiae, loss of weight, reduced activity, and fever. All control animals succumbed, with clinical signs first noted on day 7 or 8, and deaths occurring on days 9 or 10 postchallenge.

TABLE 2

Survival of replicon-inoculated cynomolgus monkeys*

| Replicon[a] | Survival/Total | Sick/Total | Day of Death |
|---|---|---|---|
| GP | 3/3★ | 0/3 | — |
| NP | 2/3 | 3/3 | 8 |
| GP + NP | 3/3★ | 0/3 | — |
| Influenza HA | 0/3 | 3/3 | 9, 9, 10 |

*surviving animals remain healty >90 days postchallenge.
[a]Antigen delivered by VEE replicon.
★Indicates p = 0.05.

Figure 3:
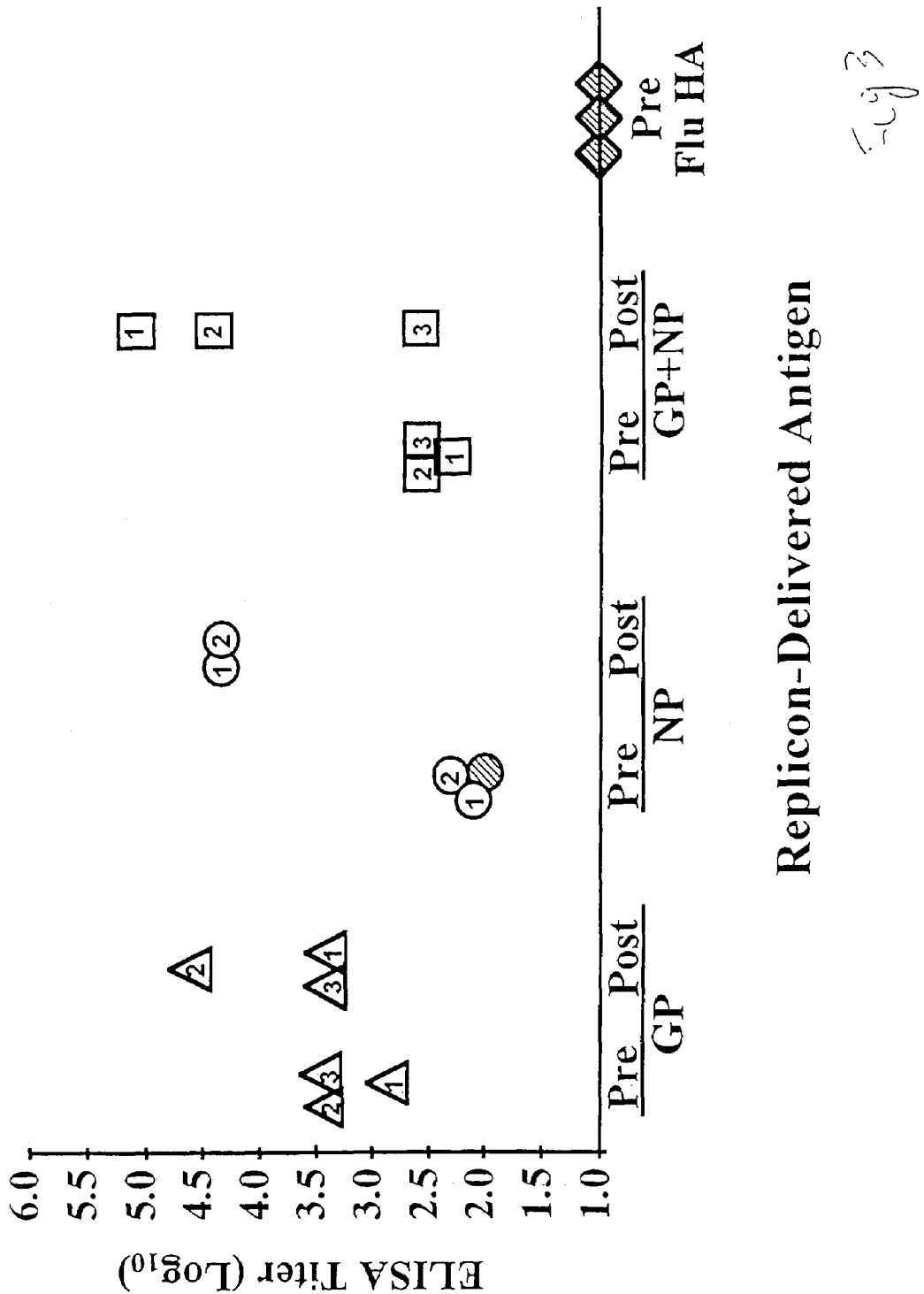
FIG. 3 Anti-MBGV ELISA titers of cynomolgus monkeys after three inoculations with recombinant replicon 17 days before or after challenge with MBGV. Prechallenge samples were obtained 17 days before challenge, while postchallenge samples were obtained 17 days after challenge. GP, animals inoculated with VEE replicons expressing MBGV GP; NP, animals inoculated with VEE replicon expressing MBGV NP; GP+NP, animals inoculated with a mixture of VEE replicons expressing either MBGV GP or NP; Flu HA, animals inoculated with VEE replicon expressing influenza HA. Numbers inside each symbol represent the same individual in each group. Symbols filled in with cross hatch marks signify animals that died from infection.

The pre- and postchallenge ELISA antibody titers of the cynomolgus macaques are shown in FIG. 3. All animals inoculated with replicons that expressed MBGV proteins demonstrated prechallenge ELISA titers to purified MBGV antigen. Of the three GP-vaccinated animals that survived challenge, two demonstrated a modest boost in ELISA antibody titer (10-30 fold) when pre- and postchallenge samples were compared. The two surviving NP-inoculated macaques had larger boosts in ELISA antibody titers (100-300 fold) when pre- and postchallenge samples were compared. Two of three animals vaccinated with both GP and NP also demonstrated 100- to 300-fold rise in ELISA titers. These observations, in conduction with the back titration of the MBGV challenge inoculum (8000 PFU), confirmed that all groups were unambiguously challenged, and that two monkeys had particularly robust immunity that apparently restricted virus replication below an immunogenic threshold.

A plaque reduction neutralization assay was performed on pre- and postchallenge serum samples. No neutralization activity was observed, at 1:20 or higher dilutions, in any sample. It should be noted that it is frequently difficult to demonstrate filovirus neutralizing antibody in vitro; however, antibodies may nonetheless be relevant in vivo (Hevey et al., 1997, *Virology* 239, 206-216), perhaps via mechanisms other than classical neutralization (Schmaljohn et al., 1982, supra).

Figure 4:
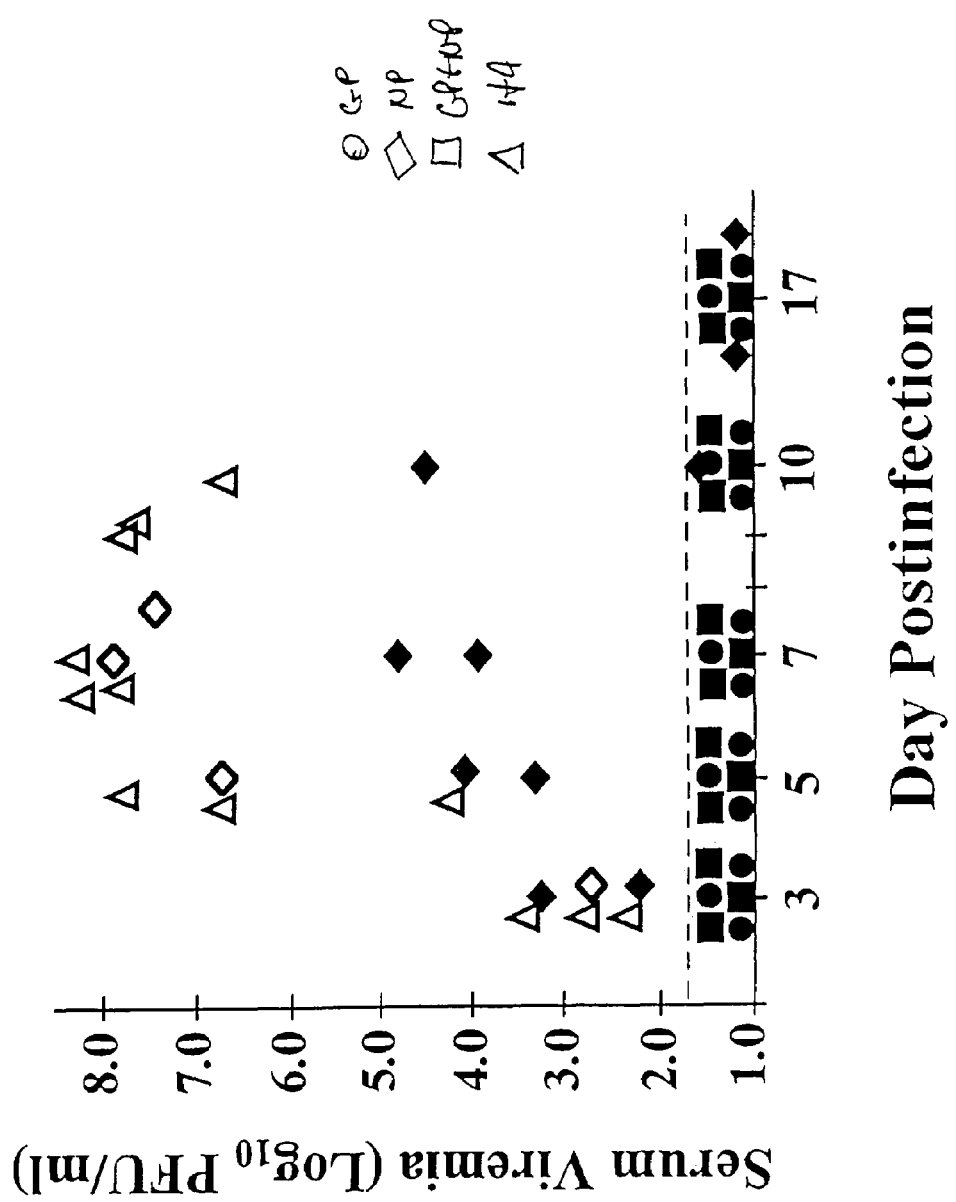
FIG. 4 Viremia level in cynomolgus monkeys inoculated with alphavirus replicons followed by challenge with MBGV (Musoke). ● Animals vaccinated with VEE replicons expressing MBGV GP; ♦ animals. vaccinated with VEE replicons expressing MBGV NP; ■, animals vaccinated with a mixture of VEE replicons which expressed either MBGV GP or NP; Δ, animals vaccinated with VEE replicons expressing influenza HA. Open symbols represent animals that died. Closed symbols represent animals that lived. Dotted line notes the lower limit of detection of this plaque assay (1.7$Log_{10}$ PFU/ml)

The viremia levels in each of the monkeys at several time points after MBGV challenge are shown in FIG. 4. The data illustrate the profound differences between lethally infected control animals and healthy survivors. Most striking, none of the animals vaccinated with GP, either alone or in combination with NP, had infectious MBGV virus in their sera that was detectable by plaque assay. Animals vaccinated with a replicon expressing influenza HA were all viremic by day 3 postchallenge and demonstrated sharp rises in MBGV viremia levels which peaked at 7.5-8.0 $Log_{10}$ PFU/ml on day 7 postinfection. Among monkeys vaccinated with NP, one died with viremias indistinguishable from controls. In contrast, the two NP-vaccinated monkeys that recovered had peak viremias that were diminished $\geq 1000$ fold compared with controls. By day 10 postinfection, the NP-vaccinated monkey with the milder illness had no detectable viremia, while the more severely affected monkey still had ~4.5 $Log_{10}$ PFU/ml virus. By day 17 postinfection no viremia was detectable in either of the surviving NP vaccinated animals.

EXAMPLE 4

Additional Measures of Vaccine-Mediated Protection

Figure 5:
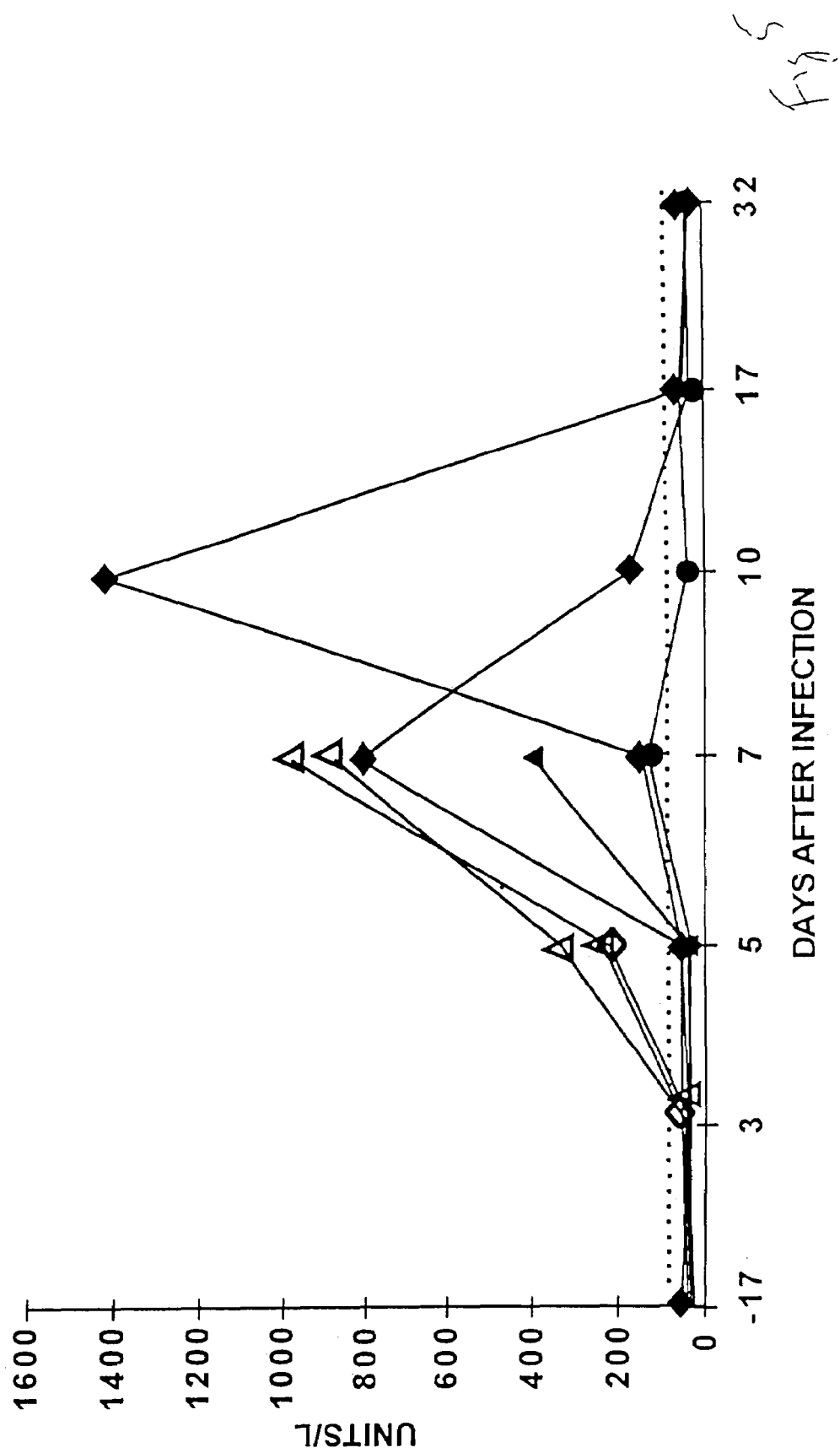
FIG. 5. Serum AST levels in VEE replicon inoculated cynomolgus macaques after challenge with MBGV (Musoke). ● The one animal (of six) vaccinated with VEE replicons expressing MBGV GP that exhibited AST abnormality at any time point. ♦, animals vaccinated with VEE replicons expressing MBGV NP; Δ, animals vaccinated with VEE replicon expressing influenza HA. Open symbols represent animals that died. Closed symbols represent animals that lived. Dotted line demarks 88 U/L, which is the mean (38 U/L) plus three standard deviations of pre-bleed values from the 12 monkeys in this experiment.

Upon necropsy of the control and the unprotected NP-inoculated monkeys, MBGV titers in their livers were 9.2, 9.7, 9.4, and 9.6 $Log_{10}$ PFU/gm. Virus was detected in all other organs examined as well, and although abundant, was at least 10-fold lower than in the liver. Not surprisingly, elevated liver enzymes were the most obvious abnormal feature in clinical chemistries. As shown in FIG. 5, unprotected monkeys had elevated AST levels by day 5 or 7 postinfection, and these were paralleled by similarly profound increases in ALT and ALP (not shown). Terminal samples were automatically rejected by the instrument as too lipemic or hemolyzed; however, in a previous set of control monkeys liver enzymes had continued to ascend dramatically (not shown). With regard to vaccine-mediated protection, it is instructive that the two NP-inoculated survivors exhibited marked but transient rises in their liver enzymes (FIG. 5), which is consistent with their viremias and signs of MBGV disease. Also, the more severely affected NP- inoculated survivor exhibited a transient rise in urea nitrogen and creatinine (not shown), coincident with recovery and viral clearance. This may have been due to virus-antibody complexes perturbing kidney function, or to direct viral damage to the organs. In contrast, the six monkeys vaccinated with GP exhibited either a minimal rise at one time point (i.e., the one GP animal shown in FIG. 5) or no significant increases in liver enzymes at any time evaluated. Other clinical chemistries and hematological findings remained normal in MBGV-inoculated macaques vaccinated previously with GP or GP+NP, in contrast with control monkeys Discussion To our knowledge, this is the first report of any filovirus vaccine shown to be completely efficacious in nonhuman primates. Before these observations, we were cautiously optimistic about the overall feasibility of an efficacious vaccine for MBGV, but were also concerned that proofs of filovirus vaccine concepts in guinea pigs may not necessarily forecast success in nonhuman primates and, by inference, in humans. Results presented here defined GP, possibly in combination with NP, as candidate antigens for a MBGV vaccine, and demonstrated that nearly complete immunity is achievable in nonhuman primates.

We chose an alphavirus replicon based on VEE virus to deliver the antigens of interest. This method of vaccination has several advantages (Pushko et al., 1997, *Virology* 239, 389-401), including the ability to produce large quantities of antigen in situ, so that native processing of the antigens might evoke a broad array of immune responses. In addition, all transcription of RNA occurs in the cytoplasm of cells, which avoids RNA splicing problems sometimes observed when proteins of RNA viruses are expressed from the nucleus. Moreover, VEE replicons have proven stable after packaging into VRPs. In addition to robust antibody induction, alphavirus replicons have been demonstrated to elicit cytotoxic T lymphocytes in mice (Caley et al., 1997, *J. Virol.* 71, 3031-3038; Zhou et al., 1995, *Proc. Natl. Acad. Sci. U.S.A.* 92, 3009-3013). The success reported here using VEE replicons to vaccinate monkeys against lethal MBGV challenge justifies a more detailed analysis of the potential of these vectors for use as human vaccines. These analyses may include such factors as the relevance of host-vector interactions that may affect vaccine potency, overall safety of the vector, and the duration and minimal requirements for immunity to MBGV disease induced by this vector.

Two viral antigens demonstrated unambiguous potential as protective antigens in the guinea pig model: MBGV GP and MBGV NP. Another viral antigen, VP35, provided significant protection from death; however, most (5/6) animals vaccinated with VP35 exhibited viremias 7 days after infection. Consequently, VP35 was not considered a candidate for the initial examination of vaccine efficacy in nonhuman primates. While none of the other viral antigens showed significant promise as protective antigens in the guinea pig model, some were only weakly immunogenic, at least when delivered as VRPs. Thus, we have not formally excluded the possibility that such antigens may prove protective under different circumstances, or in species other than guinea pigs.

As a more definitive test of efficacy, the two most promising guinea pig protective antigens from MBGV were used to inoculate nonhuman primates either alone or in combination. Using recombinant VEE replicons, MBGV GP was clearly shown to be protective. The observation that none of the animals developed overt illness or viremia was conclusive proof that this vaccine approach had protected animals from a substantial challenge dose of MBGV. However, there were some significant differences observed between guinea pigs and cynomolgus macaques. Most notable was the observation that two-thirds of the GP-vaccinated monkeys demonstrated rises in ELISA antibody titers following MBGV challenge, whereas there was apparently sterile immunity (i.e. no further increases in antibody titers) to viral challenge in guinea pigs given a 10-fold lower dose of the same vaccine. This may be attributable to the overall higher prechallenge ELISA antibody titers observed in guinea pigs when compared to those observed in the monkeys (Table 1 vs. FIG. 3).

The second antigen examined, MBGV NP, was less effective at protecting nonhuman primates compared to guinea pigs. All the monkeys inoculated with NP displayed signs of illness, with one animal dying in the same time frame as control animals. All animals were viremic, and viremia levels were predictive of outcome. As expected, the two animals that survived illness had large boosts in their ELISA antibody titers against MBGV when pre- and postchallenge sera were examined. Though not statistically significant in a group of only three animals, MBGV NP was apparently able to provide a measure of protection from death, but not from disease in two monkeys. We surmise that the immune response to NP was sufficient to suppress replication of MBGV until augmented by additional host immune responses.

The monkeys that were vaccinated with both MBGV GP and NP demonstrated the same degree of protection as the animals vaccinated with GP alone. No viremias were observed at any time point, and two of three animals demonstrated postchallenge increases in ELISA antibody titers to MBGV. These results demonstrated that the, NP replicon, equivocal by itself as a macaque vaccine, did not interfere with a GP-based vaccine when protective efficacy was used as a measurement.

For these studies, in the interest of expedient vaccine development, protection from viral disease was prioritized over the detailed study of immune mechanisms in two relatively difficult animal species for immunological studies, guinea pigs and cynomolgus macaques. It was already clear from studies done in guinea pigs that ELISA antibody titers to MBGV were not wholly predictive of clinical outcome, but rather one measure of immunogenicity of the vaccine candidate. However, it was also known that administration of polyclonal antisera or a neutralizing MAb could protect some guinea pigs from lethal challenge, indicating that antibodies can play a role in the protective response to MBGV (Hevey et al., 1997, supra). As for immunity to virtually all viruses, T cell responses to MBGV are almost certainly important in their immunoregulatory and effector functions. Indeed, we observed protection in both guinea pigs (NP and VP35) and nonhuman primates (NP) with antigens for which the most logical protective mechanisms involve cellular immunity. However, it also proved emphatically true in the most susceptible animals—nonhuman primates—that protective immunity was elicited by an antigen (GP) that theoretically favored a redundant protective response of both T cells and antibodies.

What is claimed is:

1. A method for producing Marburg virus proteins comprising culturing a eukaryotic host cell transformed with a recombinant DNA construct comprising
   (i) a Venezuelan equine encephalitis replicon vector, and
   (ii) at least one DNA fragment encoding any one of the Marburg virus proteins VP40, VP35, VP30, and VP24,
under conditions such that said DNA fragment is expressed and said Marburg virus protein is produced.

2. The method of claim 1, wherein the recombinant DNA construct is pRep Mus VP40.

3. The method of claim 1, wherein the recombinant DNA construct is pRep Mus VP35.

4. The method of claim 1, wherein the recombinant DNA construct is pRep Mus VP30.

5. The method of claim 1, wherein the recombinant DNA construct is pRep Mus VP24.

* * * * *